(12) United States Patent
Noonan et al.

(10) Patent No.: US 9,949,749 B2
(45) Date of Patent: Apr. 24, 2018

(54) OBJECT CAPTURE WITH A BASKET

(71) Applicant: Auris Surgical Robotics, Inc., San Carlos, CA (US)

(72) Inventors: David P. Noonan, San Carlos, CA (US); Joseph A. Urban, Jr., San Carlos, CA (US); Varun Agrawal, San Carlos, CA (US)

(73) Assignee: Auris Surgical Robotics, Inc., Redwood City, CA (US)

( * ) Notice: Subject to any disclaimer, the term of this patent is extended or adjusted under 35 U.S.C. 154(b) by 0 days.

(21) Appl. No.: 15/339,476

(22) Filed: Oct. 31, 2016

(65) Prior Publication Data

US 2017/0119412 A1   May 4, 2017

Related U.S. Application Data

(60) Provisional application No. 62/248,737, filed on Oct. 30, 2015.

(51) Int. Cl.
*A61B 17/221* (2006.01)
*A61B 1/307* (2006.01)
(Continued)

(52) U.S. Cl.
CPC .......... *A61B 17/221* (2013.01); *A61B 1/018* (2013.01); *A61B 1/307* (2013.01);
(Continued)

(58) Field of Classification Search
CPC .......... A61B 17/221; A61B 2017/2212; A61B 2017/2215; A61B 2017/2217;
(Continued)

(56) References Cited

U.S. PATENT DOCUMENTS

| 4,198,960 A | 4/1980 | Utsugi |
| 4,685,458 A | 8/1987 | Leckrone |

(Continued)

OTHER PUBLICATIONS

PCT Invitation to Pay Additional Fees, PCT Application No. PCT/US2016/059686, Dec. 8, 2016, 2 pages.
(Continued)

*Primary Examiner* — Dianne Dornbusch
(74) *Attorney, Agent, or Firm* — Knobbe Martens Olson & Bear LLP

(57) ABSTRACT

A method for capturing an object in a cavity in a patient is described. The method includes advancing a ureteroscope into the cavity containing the object. A basket is advanced through a working channel of the ureteroscope. The basket is opened within the cavity and is positioned so as to enclose the object. Then, two actions are performed simultaneously. The basket is collapsed while simultaneously the basket tool is advanced forward so that the object remains within the basket, ideally near the center of the basket, as the basket closes around the object. Once the object is captured, the basket is retracted to remove the object out of the cavity. Further, this process may be automated by having the method carried out by robotic arms acting in tandem, with one or more robotic arms advancing the basket tool or ureteroscope, and another robotic arm collapsing the basket.

27 Claims, 25 Drawing Sheets

(51) Int. Cl.
*A61B 1/018* (2006.01)
*A61B 17/3203* (2006.01)
*A61B 34/00* (2016.01)
*A61B 18/26* (2006.01)
*A61B 34/30* (2016.01)
*A61B 17/3207* (2006.01)
*A61B 18/00* (2006.01)

(52) U.S. Cl.
CPC .......... *A61B 17/32037* (2013.01); *A61B 17/320758* (2013.01); *A61B 18/26* (2013.01); *A61B 34/30* (2016.02); *A61B 34/71* (2016.02); *A61B 2017/2212* (2013.01); *A61B 2017/2215* (2013.01); *A61B 2018/00511* (2013.01); *A61B 2018/00517* (2013.01); *A61B 2034/301* (2016.02); *A61B 2034/302* (2016.02); *A61B 2217/005* (2013.01)

(58) Field of Classification Search
CPC .......... A61B 34/30; A61B 2034/301; A61B 2034/302; A61B 2034/303
See application file for complete search history.

(56) References Cited

U.S. PATENT DOCUMENTS

| | | | |
|---|---|---|---|
| 4,747,405 A | 5/1988 | Leckrone | |
| 4,898,574 A | 2/1990 | Uchiyama | |
| 5,372,124 A * | 12/1994 | Takayama | A61B 10/06 414/4 |
| 5,450,843 A | 9/1995 | Moll | |
| 5,472,426 A | 12/1995 | Bonati | |
| 5,645,083 A | 7/1997 | Essig | |
| 5,924,175 A * | 7/1999 | Lippitt | A61B 17/221 24/537 |
| 6,440,061 B1 | 8/2002 | Wenner | |
| 6,706,050 B1 | 3/2004 | Giannadakis | |
| 9,592,042 B2 | 3/2017 | Titus | |
| 2002/0068954 A1 | 6/2002 | Foster | |
| 2004/0122444 A1 | 6/2004 | Gerard | |
| 2004/0158261 A1 | 8/2004 | Vu | |
| 2005/0261705 A1 | 11/2005 | Gist | |
| 2006/0058813 A1 * | 3/2006 | Teague | A61B 17/221 606/113 |
| 2006/0116693 A1 * | 6/2006 | Weisenburgh, II | A61B 17/12099 606/128 |
| 2006/0135963 A1 | 6/2006 | Kick | |
| 2007/0250111 A1 * | 10/2007 | Lu | A61B 17/221 606/205 |
| 2009/0082634 A1 | 3/2009 | Kathrani | |
| 2011/0015483 A1 * | 1/2011 | Barbagli | A61B 1/307 600/108 |
| 2011/0071541 A1 | 3/2011 | Prisco | |
| 2011/0071543 A1 | 3/2011 | Prisco | |
| 2013/0066136 A1 * | 3/2013 | Palese | A61B 17/52 600/11 |
| 2013/0253267 A1 * | 9/2013 | Collins | A61B 17/221 600/104 |
| 2013/0303876 A1 | 11/2013 | Gelfand | |
| 2014/0058404 A1 * | 2/2014 | Hammack | A61B 17/221 606/127 |
| 2014/0163318 A1 | 6/2014 | Swanstrom | |
| 2014/0309655 A1 | 10/2014 | Gal | |
| 2014/0316203 A1 * | 10/2014 | Carroux | A61B 1/00133 600/146 |
| 2016/0022289 A1 | 1/2016 | Wan | |
| 2016/0030073 A1 * | 2/2016 | Isakov | A61B 17/221 606/113 |
| 2016/0249932 A1 | 9/2016 | Rogers | |
| 2017/0065227 A1 * | 3/2017 | Marrs | A61B 5/6858 |
| 2017/0119412 A1 | 5/2017 | Noonan | |
| 2017/0119413 A1 | 5/2017 | Romo | |

OTHER PUBLICATIONS

International Search Report for International Application No. PCT/US2016/059686 dated Feb. 17, 2017.

* cited by examiner

OBJECT CAPTURE WITH A BASKET

CROSS-REFERENCE TO RELATED APPLICATIONS

This application claims the benefit of and priority to U.S. Provisional Application No. 62/248,737, filed Oct. 30, 2015, which is incorporated herein by reference.

BACKGROUND

1. Field of Art

This description generally relates to surgical robotics, and particularly to lithotomy devices and procedures using a surgical robotics system.

2. Description of the Related Art

Every year, doctors perform thousands of procedures to remove urinary stones from patients' urinary tracts. Urinary stones may include kidney stones found in the kidneys and ureters as well as bladder stones found in the bladder. Such urinary stones form as a result of concentrated minerals and cause significant abdominal pain once they reach a size sufficient to impede urine flow through the ureter or urethra. Such stones may formed from calcium, magnesium, ammonia, ur acid, cysteine, or other compounds.

To remove urinary stones from the bladder and ureter, surgeons use a ureteroscope inserted into the urinary tract through the urethra. Typically, a ureteroscope includes an endoscope at its distal end to enable visualization of the urinary tract. The ureteroscope also includes a lithotomy mechanism to capture or break apart urinary stones. During the ureteroscopy procedure, one physician controls the position of the ureteroscope and the other surgeon controls the lithotomy mechanism. The controls of the ureteroscope are located on a proximal handle of the ureteroscope and accordingly are difficult to grasp as the orientation of the ureteroscope changes. Accordingly, present ureteroscopy techniques are labor intensive and reliant on ureteroscopes with non-ergonomic designs.

To remove large kidney stones from the kidneys, surgeons use a percutaneous nephrolithotomy technique that includes inserting a nephroscope through the skin to break up and remove the kidney stone. However, present techniques for percutaneous nephrolithotomy ("PCNL") include using fluoroscopy to locate the kidney stone and to ensure accurate insertion of the nephroscope. Fluoroscopy increases the cost of the nephrolithotomy procedure due to the cost of the fluoroscope itself as well as the cost of a technician to operate the fluoroscope. Fluoroscopy also exposes the patient to radiation for a prolonged period of time. Even with fluoroscopy, accurately making a percutaneous incision to access the kidney stone is difficult and imprecise. Additionally, present nephrolithotomy techniques typically involve a two-day or three-day inpatient stay. In sum, present nephrolithotomy techniques are costly and problematic for patients.

SUMMARY

This description includes methods and devices for more easily carrying out a ureteroscopy. This description also includes methods and devices for more easily carrying out a PCNL. For ureteroscopy, a basketing device includes a number of independently manipulable pull wires that allow full 360 degree motion of the basket, which makes capture of a stone easier. A central working channel in the basketing apparatus allows a variety of other tools to be placed near a basket to break up a captured stone. Further, a technique for ureteroscopy is described that helps prevent stones from escaping from a basket while the basket is being closed.

For PCNL, a variety of techniques and devices are described that make use of an alignment sensor in place of fluoroscopy to detect the position of a stone in a kidney. The alignment sensor may, for example, be an EM sensor which works in conjunction with EM field generators placed around the patient and an associated CT (or other) scan to provide position and orientation information for EM sensor in the patient's body. The alignment sensor is placed via a cavity, such as the ureter using a ureteroscope, and together with a camera is used to identify the location of the stone. The alignment sensor provides a guidance mechanism for directing the percutaneous cut for accessing the stone within the kidney. Further, as at this point in the PCNL procedure, a scope is already present, a working channel of the scope can be used to advance other tools to assist in the removal of the stone through a port created by the PCNL. Techniques for performing the PCNL are described, as well as for how to go about removing the stone via the PCNL port.

Although this description is largely described with respect to the example use cases of ureteroscopy, PCNL, and the removal of urinary stones and stone fragments, these descriptions are equally applicable to other surgical operations concerned with the removal of objects from the patient, including any object that can be safely removed via a patient cavity (e.g., the esophagus, ureter, intestine, etc.) or via percutaneous access, such as gallbladder stone removal or lung (pulmonary/transthoracic) tumor biopsy.

Reference will now be made in detail to several embodiments, examples of which are illustrated in the accompanying figures. It is noted that wherever practicable similar or like reference numbers may be used in the figures and may indicate similar or like functionality. The figures depict embodiments of the described system (or method) for purposes of illustration only. One skilled in the art will readily recognize from the following description that alternative embodiments of the structures and methods illustrated herein may be employed without departing from the principles described herein.

DETAILED DESCRIPTION

I. Overview

I.A. Surgical Robotics System

Figure 1A:
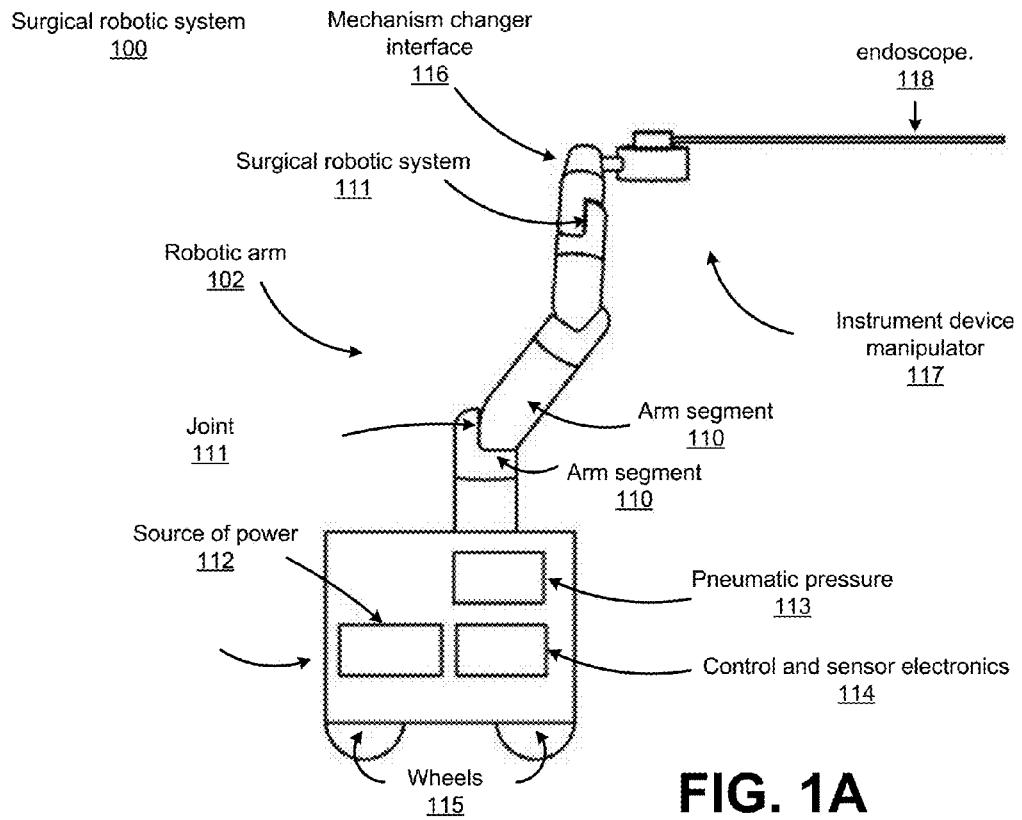
FIG. 1A shows an example surgical robotic system, according to one embodiment.

FIG. 1A shows an example surgical robotic system 100, according to one embodiment. The surgical robotic system 100 includes a base 101 coupled to one or more robotic arms, e.g., robotic arm 102. The base 101 is communicatively coupled to a command console, which is further described with reference to FIG. 2. The base 101 can be positioned such that the robotic arm 102 has access to perform a surgical procedure on a patient, while a user such as a physician may control the surgical robotic system 100 from the comfort of the command console. In some embodiments, the base 101 may be coupled to a surgical operating table or bed for supporting the patient. Though not shown in FIG. 1 for purposes of clarity, the base 101 may include subsystems such as control electronics, pneumatics, power sources, optical sources, and the like. The robotic arm 102 includes multiple arm segments 110 coupled at joints 111, which provides the robotic arm 102 multiple degrees of freedom, e.g., seven degrees of freedom corresponding to seven arm segments. The base 101 may contain a source of power 112, pneumatic pressure 113, and control and sensor electronics 114—including components such as a central processing unit, data bus, control circuitry, and memory—and related actuators such as motors to move the robotic arm 102. The electronics 114 in the base 101 may also process and transmit control signals communicated from the command console.

In some embodiments, the base 101 includes wheels 115 to transport the surgical robotic system 100. Mobility of the surgical robotic system 100 helps accommodate space constraints in a surgical operating room as well as facilitate appropriate positioning and movement of surgical equipment. Further, the mobility allows the robotic arms 102 to be configured such that the robotic arms 102 do not interfere with the patient, physician, anesthesiologist, or any other equipment. During procedures, a user may control the robotic arms 102 using control devices such as the command console.

In some embodiments, the robotic arm 102 includes set up joints that use a combination of brakes and counter-balances to maintain a position of the robotic arm 102. The counter-balances may include gas springs or coil springs. The brakes, e.g., fail safe brakes, may be include mechanical and/or electrical components. Further, the robotic arms 102 may be gravity-assisted passive support type robotic arms.

Each robotic arm 102 may be coupled to an instrument device manipulator (IDM) 117 using a mechanism changer interface (MCI) 116. The IDM 117 can be removed and replaced with a different type of IDM, for example, a first type of IDM manipulates an endoscope, while a second type of IDM manipulates a laparoscope. The MCI 116 includes connectors to transfer pneumatic pressure, electrical power, electrical signals, and optical signals from the robotic arm 102 to the IDM 117. The MCI 116 can be a set screw or base plate connector. The IDM 117 manipulates surgical instruments (also referred to as surgical tools) such as the endoscope 118 using techniques including direct drive, harmonic drive, geared drives, belts and pulleys, magnetic drives, and the like. The MCI 116 is interchangeable based on the type of IDM 117 and can be customized for a certain type of surgical procedure. The robotic 102 arm can include a joint level torque sensing and a wrist at a distal end, such as the KUKA AG® LBR5 robotic arm.

An endoscope 118 is a tubular and flexible surgical instrument that is inserted into the anatomy of a patient to capture images of the anatomy (e.g., body tissue). In particular, the endoscope 118 includes one or more imaging devices (e.g., cameras or other types of optical sensors) that capture the images. The imaging devices may include one or more optical components such as an optical fiber, fiber array, or lens. The optical components move along with the tip of the endoscope 118 such that movement of the tip of the endoscope 118 results in changes to the images captured by the imaging devices. An example endoscope 118 is further described with reference to FIGS. 3A-4B in Section IV. Endoscope.

Robotic arms 102 of the surgical robotic system 100 manipulate the endoscope 118 using elongate movement members. The elongate movement members may include pull wires, also referred to as pull or push wires, cables, fibers, or flexible shafts. For example, the robotic arms 102 actuate multiple pull wires coupled to the endoscope 118 to deflect the tip of the endoscope 118. The pull wires may include both metallic and non-metallic materials such as stainless steel, Kevlar, tungsten, carbon fiber, and the like. The endoscope 118 may exhibit nonlinear behavior in response to forces applied by the elongate movement members. The nonlinear behavior may be based on stiffness and compressibility of the endoscope 118, as well as variability in slack or stiffness between different elongate movement members.

Figure 1B:
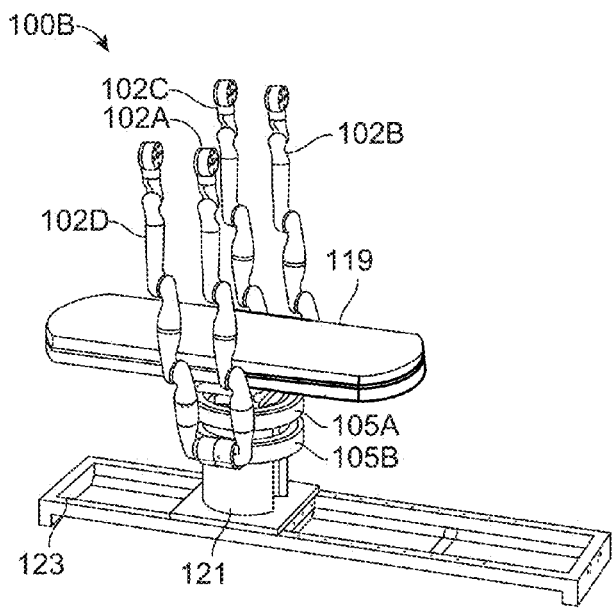
FIG. 1B is a perspective view of a surgical robotics system with column-mounted robotic arms according to one embodiment.

FIG. 1B is a perspective view of a surgical robotics system 100A with column-mounted robotic arms according to one embodiment. The surgical robotics system 100A includes a set of robotic arms 102, a set of column rings, table 119, column 121, and base 123.

The table 119 provides support for a patient undergoing surgery using the surgical robotics system 100. Generally, the table 119 is parallel to the ground, though the table 119 may change its orientation and configuration to facilitate a variety of surgical procedures. The table may be rotated around the patient's transverse axis or tilted along the patient's longitudinal axis using one or more pivots between the table 119 and the column 121. The table 119 may include swivel segments, foldable segments, or both to change the configuration of an upper surface of the table 119 that supports the patient. The table 119 may include a trapdoor to facilitate drainage of bodily fluids or other ensuing fluids during surgical procedures.

The column 121 is coupled to the table 119 on one end and coupled to the base 123 on the other end. Generally, the column 121 is cylindrically shaped to accommodate one or more column rings 105 coupled to the column 121; however, the column 121 may have other shapes such as oval or rectangular. A column ring 105 is movably coupled to the column. For example, a column ring 105 translates vertically along the axis of the column 121, rotates horizontally around the axis of the column 121, or both. Column rings 105 are described in more detail with respect to FIG. 2 below. The column may be rotated around the column's central axis relative to the base 123 using a rotation mechanism.

The base 123 is parallel to the ground and provides support for the column 121 and the table 119. The base 123 may include wheels, treads, or other means of positioning or transporting the surgical robotics system 100. The base 123 may accommodate the set of robotic arms 102, the one or more column rings 105, or both as part of an inactive configuration for storage, such as inside a removable housing (not shown). The base 123 may include rails (not shown) along which robotic arms 102 may be movably coupled as an alternative or supplement to column rings 105.

Generally, the set of robotics arms includes one or more robotic arms 102 coupled to one or more column rings 105, such as column ring 105A. A robotic arm 102 attached to a column 105 may be referred to as a column-mounted robotic arm 102. The surgical robotics system 100A uses robotic arms 102 to perform surgical procedures on a patient lying on the table 119.

Further details and configurations regarding table 119, column 121, base 123, column ring 105, and robotic arm 102 are included in U.S. patent application Ser. No. 15/154,765, filed May 13, 2016, as well as in U.S. patent application Ser. No. 15/154,762, filed May 13, 2016, each of which is incorporated by reference herein. For example, an alternative surgical robotics system includes a first robotic arm 102 mounted to a column ring 105 and a second robotic arm mounted to a rail included in the base 123.

Figure 2:
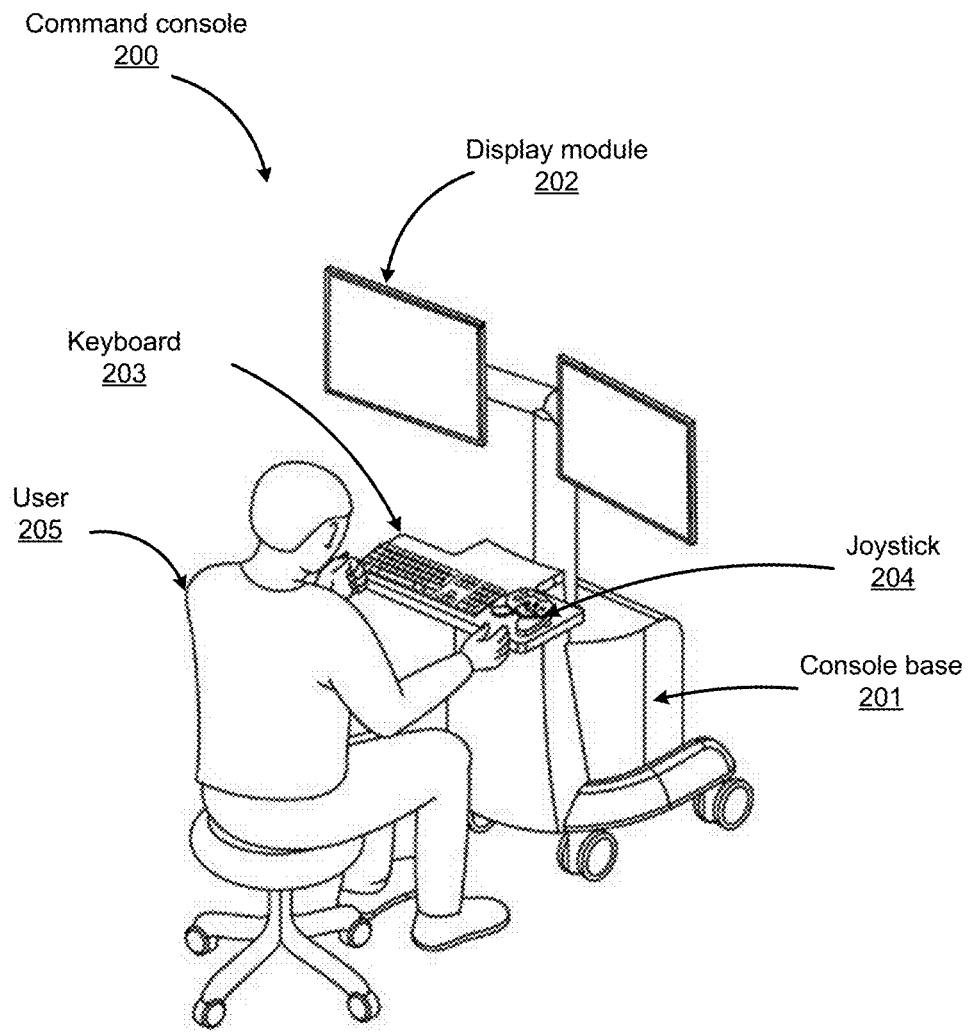
FIG. 2 shows an example command console for the example surgical robotic system 100, according to one embodiment.

FIG. 2 shows an example command console 200 for the example surgical robotic system 100, according to one embodiment. The command console 200 includes a console base 201, display modules 202, e.g., monitors, and control modules, e.g., a keyboard 203 and joystick 204. In some embodiments, one or more of the command console 200 functionality may be integrated into a base 101 of the surgical robotic system 100 or another system communicatively coupled to the surgical robotic system 100. A user 205, e.g., a physician, remotely controls the surgical robotic system 100 from an ergonomic position using the command console 200.

The console base 201 may include the basic components of a computer system, that is a central processing unit (i.e., a computer processer), a memory/data storage unit, a data bus, and associated data communication ports that are responsible for interpreting and processing signals such as imagery and alignment sensor data, e.g., from the endoscope 118 shown in FIG. 1. In some embodiments, both the console base 201 and the base 101 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, trackpads, trackballs, control pads, video game controllers, and sensors (e.g., motion sensors or cameras) that capture hand gestures and finger gestures.

The user 205 can control a surgical instrument such as the endoscope 118 using the command console 200 in a velocity mode or position control mode. In velocity mode, the user 205 directly controls pitch and yaw motion of a distal end of the endoscope 118 based on direct manual control using the control modules. For example, movement on the joystick 204 may be mapped to yaw and pitch movement in the distal end of the endoscope 118. The joystick 204 can provide haptic feedback to the user 205. For example, the joystick 204 vibrates to indicate that the endoscope 118 cannot further translate or rotate in a certain direction. The command console 200 can also provide visual feedback (e.g., pop-up messages) and/or audio feedback (e.g., beeping) to indicate that the endoscope 118 has reached maximum translation or rotation.

In position control mode, the command console 200 uses a three-dimensional (3D) map of a patient and pre-determined computer models of the patient to control a surgical instrument, e.g., the endoscope 118. The command console 200 provides control signals to robotic arms 102 of the surgical robotic system 100 to manipulate the endoscope 118 to a target location. Due to the reliance on the 3D map, position control mode requires accurate mapping of the anatomy of the patient.

In some embodiments, users 205 can manually manipulate robotic arms 102 of the surgical robotic system 100 without using the command console 200. During setup in a surgical operating room, the users 205 may move the robotic arms 102, endoscopes 118, and other surgical equipment to access a patient. The surgical robotic system 100 may rely on force feedback and inertia control from the users 205 to determine appropriate configuration of the robotic arms 102 and equipment.

The display modules 202 may include electronic monitors, virtual reality viewing devices, e.g., goggles or glasses, and/or other means of display devices. In some embodiments, the display modules 202 are integrated with the control modules, for example, as a tablet device with a touchscreen. Further, the user 205 can both view data and input commands to the surgical robotic system 100 using the integrated display modules 202 and control modules. The display modules 202 allow for display of graphical GUIs that may display information about the position and orientation of various instruments operating within the patient based on information provided by one or more alignment sensors. This information may be received by electrical wires or transmitters coupled to the sensors, which transmit the information to the console base 201, which processes the information for presentation via the display modules 202.

The display modules 202 can display 3D images using a stereoscopic device, e.g., a visor or goggle. The 3D images provide an "endo view" (i.e., endoscopic view), which is a computer 3D model illustrating the anatomy of a patient. The endo view provides a virtual environment of the patient's interior and an expected location of an endoscope 118 inside the patient. A user 205 compares the endo view model to actual images captured by a camera to help mentally orient and confirm that the endoscope 118 is in the correct—or approximately correct—location within the patient. The endo view provides information about anatomical structures, e.g., the shape of an intestine or colon of the patient, around the distal end of the endoscope 118. The display modules 202 can simultaneously display the 3D model and computerized tomography (CT) scans of the anatomy the around distal end of the endoscope 118. Further, the display modules 202 may overlay the already determined navigation paths of the endoscope 118 on the 3D model and CT scans.

In some embodiments, a model of the endoscope 118 is displayed with the 3D models to help indicate a status of a surgical procedure. For example, the CT scans identify a lesion in the anatomy where a biopsy may be necessary. During operation, the display modules 202 may show a reference image captured by the endoscope 118 corresponding to the current location of the endoscope 118. The display modules 202 may automatically display different views of the model of the endoscope 118 depending on user settings and a particular surgical procedure. For example, the display modules 202 show an overhead fluoroscopic view of the endoscope 118 during a navigation step as the endoscope 118 approaches an operative region of a patient.

I.B. Endoscope

Figure 3A:
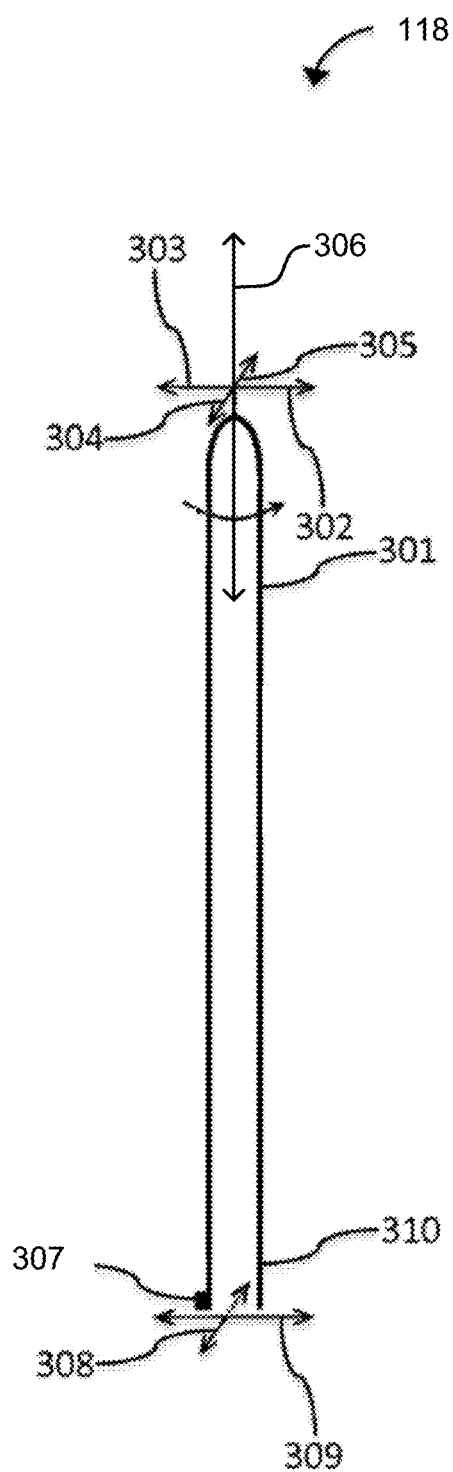
FIG. 3A illustrates multiple degrees of motion of an endoscope according to one embodiment.

FIG. 3A illustrates multiple degrees of motion of an endoscope 118 according to one embodiment. As shown in FIG. 3A, the tip 301 of the endoscope 118 is oriented with zero deflection relative to a longitudinal axis 306 (also referred to as a roll axis 306). To capture images at different orientations of the tip 301, a surgical robotic system 100 deflects the tip 301 on a positive yaw axis 302, negative yaw axis 303, positive pitch axis 304, negative pitch axis 305, or roll axis 306. The tip 301 or body 310 of the endoscope 118 may be elongated or translated in the longitudinal axis 306, x-axis 308, or y-axis 309.

The endoscope 118 includes a reference structure 307 to calibrate the position of the endoscope 118. For example, the surgical robotic system 100 measures deflection of the endoscope 118 relative to the reference structure 307. The reference structure 307 is located on a proximal end of the endoscope 118 and may include a key, slot, or flange. The reference structure 307 is coupled to a first drive mechanism for initial calibration and coupled to a second drive mechanism, e.g., the IDM 117, to perform a surgical procedure.

Figure 3B:
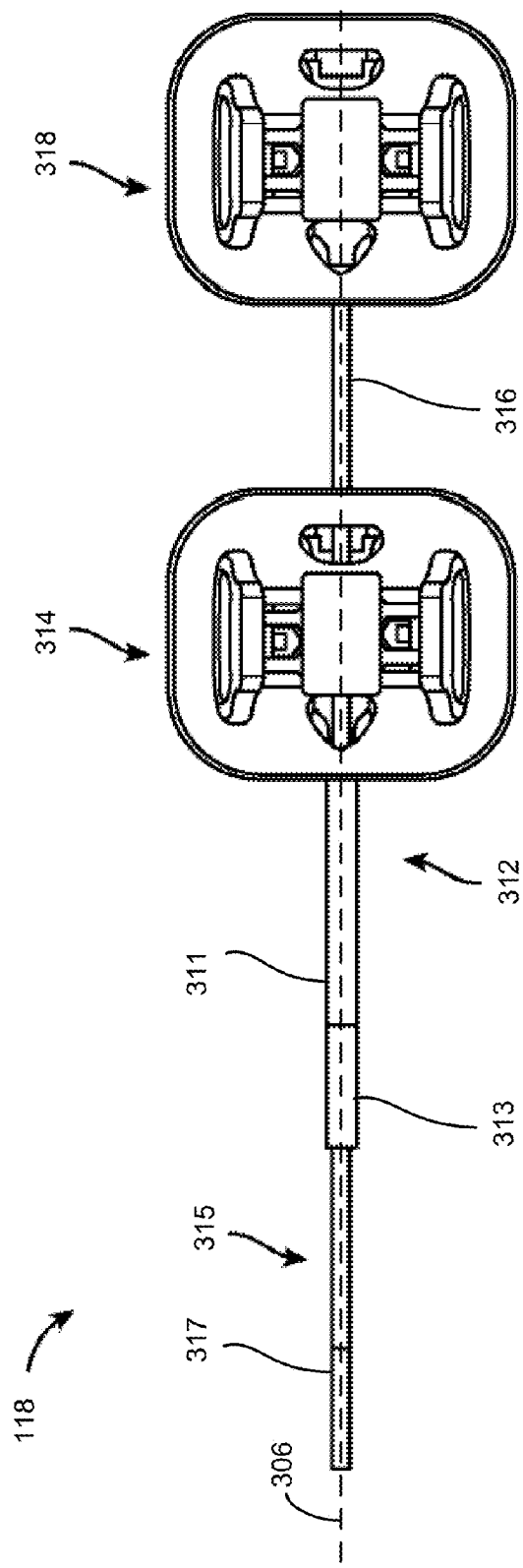
FIG. 3B is a top view of an endoscope according to one embodiment.

FIG. 3B is a top view of an endoscope 118 according to one embodiment. The endoscope 118 includes a leader 315 tubular component (or leaderscope) nested or partially nested inside and longitudinally-aligned with a sheath 311 tubular component. The sheath 311 includes a proximal sheath section 312 and distal sheath section 313. The leader 315 has a smaller outer diameter than the sheath 311 and includes a proximal leader section 316 and distal leader section 317. The sheath base 314 and the leader base 318 actuate the distal sheath section 313 and the distal leader section 317, respectively, for example, based on control signals from a user of a surgical robotic system 100. The sheath base 314 and the leader base 318 are, e.g., part of the IDM 117 shown in FIG. 1.

Both the sheath base 314 and the leader base 318 include drive mechanisms (e.g., the independent drive mechanism further described with reference to FIG. 3D in Section I.C. Instrument Device Manipulator) to control pull wires coupled to the sheath 311 and leader 315. For example, the sheath base 314 generates tensile loads on pull wires coupled to the sheath 311 to deflect the distal sheath section 313. Similarly, the leader base 318 generates tensile loads on pull wires coupled to the leader 315 to deflect the distal leader section 317. Both the sheath base 314 and leader base 318 may also include couplings for the routing of pneumatic pressure, electrical power, electrical signals, or optical signals from IDMs to the sheath 311 and leader 314, respectively. A pull wire may include a steel coil pipe along the length of the pull wire within the sheath 311 or the leader 315, which transfers axial compression back to the origin of the load, e.g., the sheath base 314 or the leader base 318, respectively.

The endoscope 118 can navigate the anatomy of a patient with ease due to the multiple degrees of freedom provided by pull wires coupled to the sheath 311 and the leader 315. For example, four or more pull wires may be used in either the sheath 311 and/or the leader 315, providing eight or more degrees of freedom. In other embodiments, up to three pull wires may be used, providing up to six degrees of freedom. The sheath 311 and leader 315 may be rotated up to 360 degrees along a longitudinal axis 306, providing more degrees of motion. The combination of rotational angles and multiple degrees of freedom provides a user of the surgical robotic system 100 with a user friendly and instinctive control of the endoscope 118.

Figure 3C:
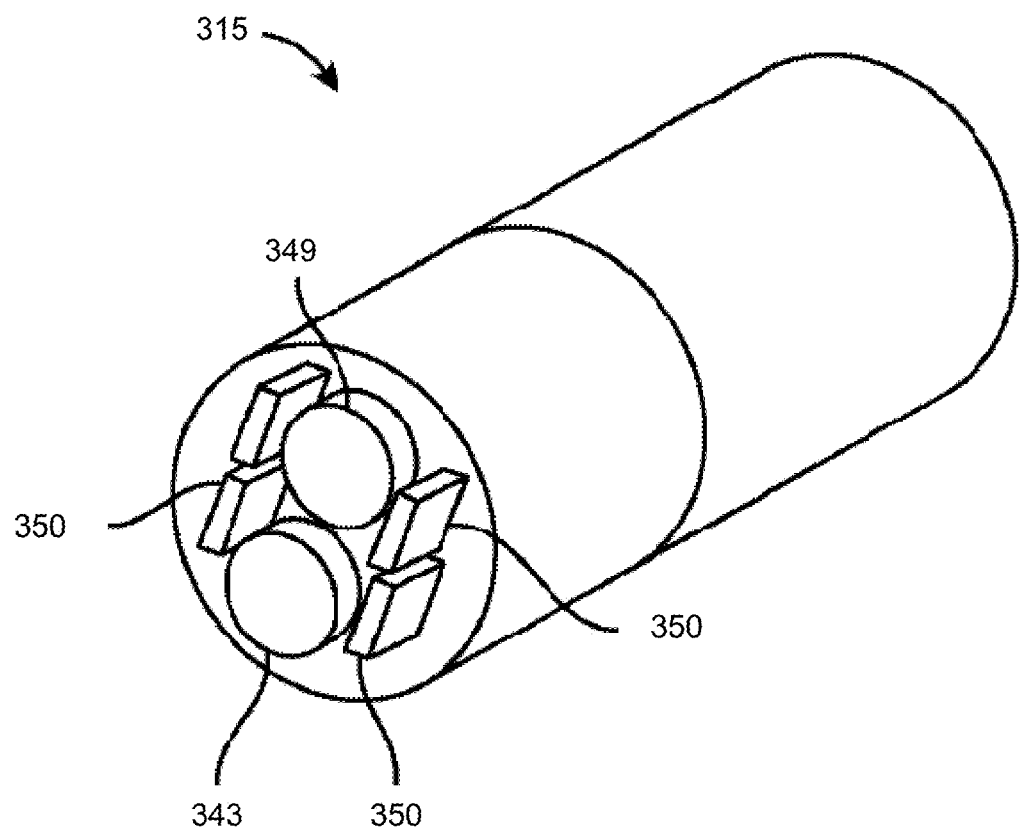
FIG. 3C is an isometric view of the distal end of the leader of an endoscope according to one embodiment.

FIG. 3C is a isometric view of the distal end of leader 315 of an endoscope 118 according to one embodiment. The leader 315 includes at least one working channel 343 and pull wires and running through conduits along the length of the walls. For example, the pull wires and may have a helix section that helps mitigate muscling and curve alignment of the leader 315. The leader 315 includes an imaging device 349 (e.g., charge-coupled device (CCD) or complementary metal-oxide semiconductor (CMOS) camera, imaging fiber bundle, etc.), light sources 350 (e.g., light-emitting diode (LED), optic fiber, etc.), and at least one working channel 343 for other components. For example, other components include camera wires, an insufflation device, a suction device, electrical wires, fiber optics, an ultrasound transducer, electromagnetic (EM) sensing components, and optical coherence tomography (OCT) sensing components. In some embodiments, the leader 315 includes a cavity that runs along the long axis of the leader 315 to form a working channel 343 which accommodates insertion of other devices such as surgical tools.

I.C. Instrument Device Manipulator

Figure 3D:
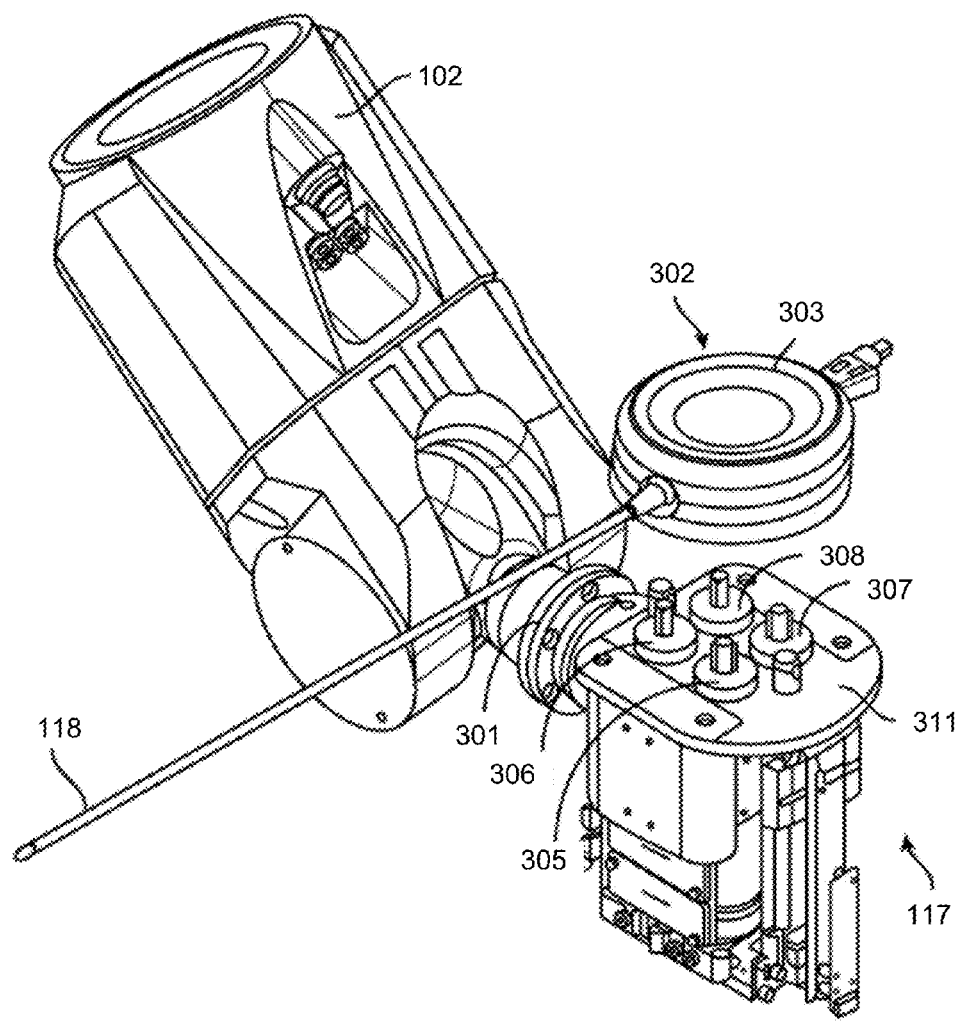
FIG. 3D is an isometric view of an instrument device manipulator of the surgical robotic system according to one embodiment.

FIG. 3D is an isometric view of an instrument device manipulator 117 of the surgical robotic system 100 according to one embodiment. The robotic arm 102 is coupled to the IDM 117 via an articulating interface 301. The IDM 117 is coupled to the endoscope 118. The articulating interface 301 may transfer pneumatic pressure, power signals, control signals, and feedback signals to and from the robotic arm 102 and the IDM 117. The IDM 117 may include a gear head, motor, rotary encoder, power circuits, and control circuits. A base 303 for receiving control signals from the IDM 117 is coupled to the proximal end of the endoscope 118. Responsive to the control signals, the IDM 117 manipulates the endoscope 118 by actuating output shafts, which are further described below with reference to FIG. 3E.

Figure 3E:
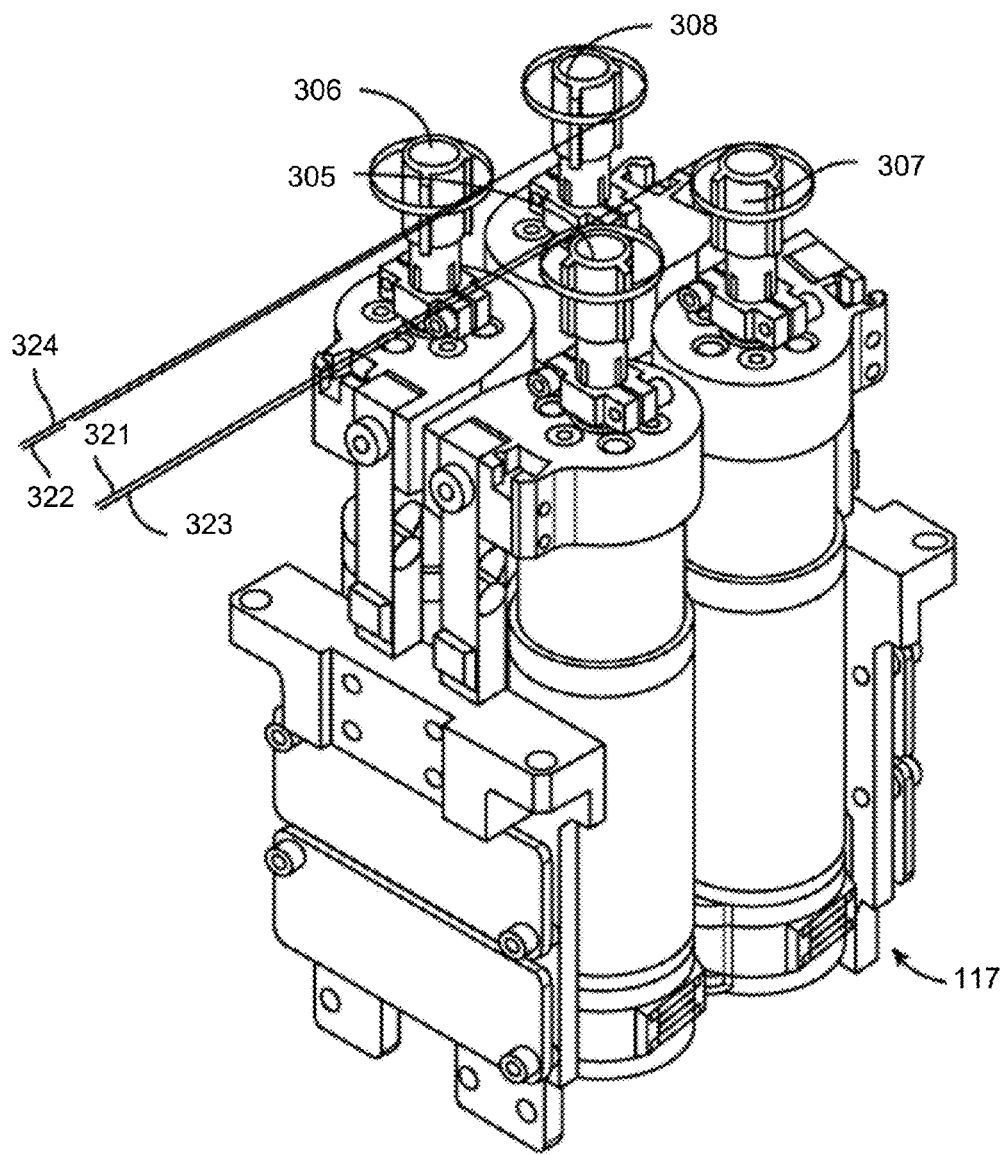
FIG. 3E is an exploded isometric view of the instrument device manipulator shown in FIG. 3D according to one embodiment.

FIG. 3E is an exploded isometric view of the instrument device manipulator shown in FIG. 3D according to one embodiment. In FIG. 3E, the endoscope 118 has been removed from the IDM 117 to reveal the output shafts 305, 306, 307, and 308 which may each control independent pull wires of an endoscope 118 or basket apparatus as described further below.

II. Lower Body Surgery

Figure 4A:
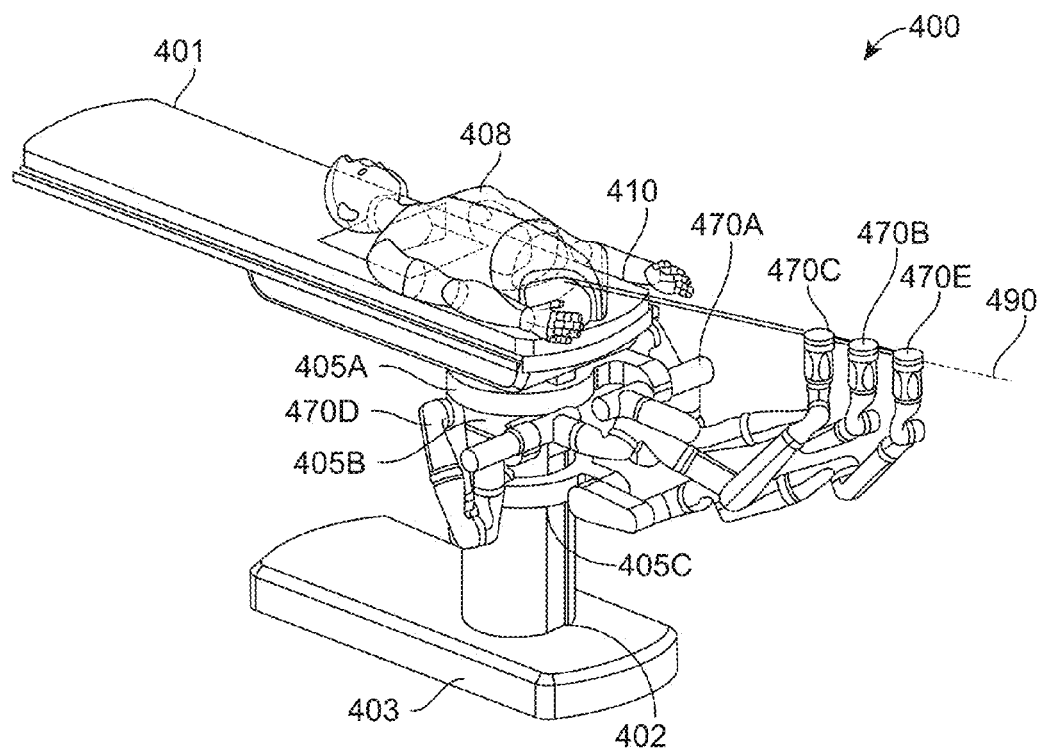
FIG. 4A is a perspective view of a surgical robotics system with column-mounted arms configured to access the lower body area of a simulated patient according to one embodiment.

FIG. 4A is a perspective view of a surgical robotics system 400A with column-mounted arms configured to access the lower body area of a simulated patient 408 according to one embodiment. The surgical robotics system 400A includes a set of robotic arms (including five robotic arms in total) and a set of three column rings. A first robotic arm 470A and a second robotic arm 470B are coupled to a first column ring 405A. A third robotic arm 470C and a fourth robotic arm 470D are coupled to a second column ring 405B. A fifth robotic arm 470E is coupled to a third column ring 405C. FIG. 4A shows a wireframe of the patient 408 lying on the table 401 undergoing a surgical procedure, e.g., ureteroscopy, involving access to the lower body area of the patient 408. Legs of the patient 408 are not shown in order to avoid obscuring portions of the surgical robotics system 400A.

The surgical robotics system 400A configures the set of robotic arms to perform a surgical procedure on the lower body area of the patient 408. Specifically, the surgical robotics system 400A configures the set of robotic arms to manipulate a surgical instrument 410. The set of robotic arms insert the surgical instrument 410 along a virtual rail 490 into the groin area of the patient 408. Generally, a virtual rail 490 is a co-axial trajectory along which the set of robotic arms translates a surgical instrument (e.g., a telescoping instrument). The second robotic arm 470B, the third robotic arm 470C, and the fifth robotic arm 470E are coupled, e.g., holding, the surgical instrument 410. The first robotic arm 470A and the fourth robotic arm 470D are stowed to the sides of the surgical robotics system because they are not necessarily required to for the surgical procedure—or at least part of the surgical procedure—shown in FIG. 4A. The robotic arms are configured such that they manipulate the surgical instrument 410 from a distance away from the patient 408. This is advantageous, for example, because there is often limited space available closer toward the patient's body or there is a sterile boundary around the patient 408. Further, there may also be a sterile drape around surgical equipment. During a surgical procedure, only sterile objects are allowed pass the sterile boundary. Thus, the surgical robotics system 400A may still use robotic arms that are positioned outside of the sterile boundary and that are covered with sterilized drapes to perform a surgical procedure.

In one embodiment, the surgical robotics system 400A configures the set of robotic arms to perform an endoscopy surgical procedure on the patient 408. The set of robotic arms hold an endoscope, e.g., the surgical instrument 410. The set of robotic arms insert the endoscope into the patient's body via an opening in the groin area of the patient 408. The endoscope is a flexible, slender, and tubular instrument with optical components such as a camera and optical cable. The optical components collect data representing images of portions inside the patient's body. A user of the surgical robotics system 400A uses the data to assist with performing the endoscopy.

Figure 4B:
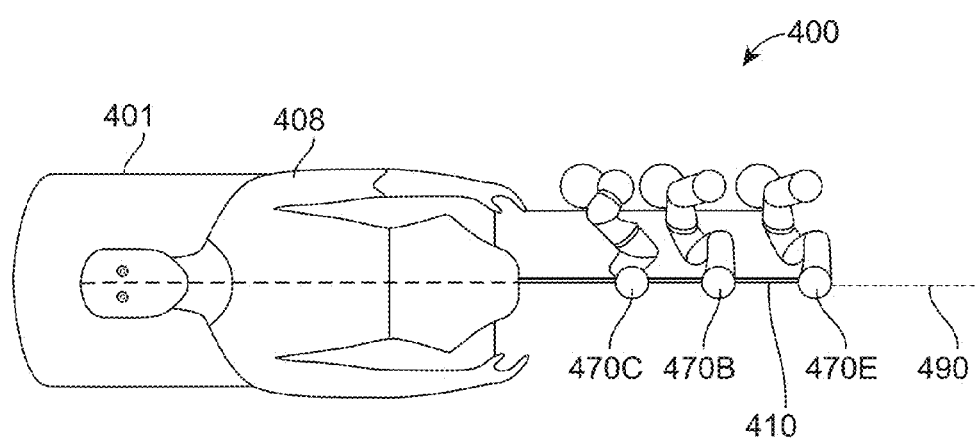
FIG. 4B is a top view of the surgical robotics system with column-mounted arms configured to access the lower body area of the simulated patient according to one embodiment.

FIG. 4B is a top view of the surgical robotics system 400A with column-mounted arms configured to access the lower body area of the patient 408 according to one embodiment.

Figure 4C:
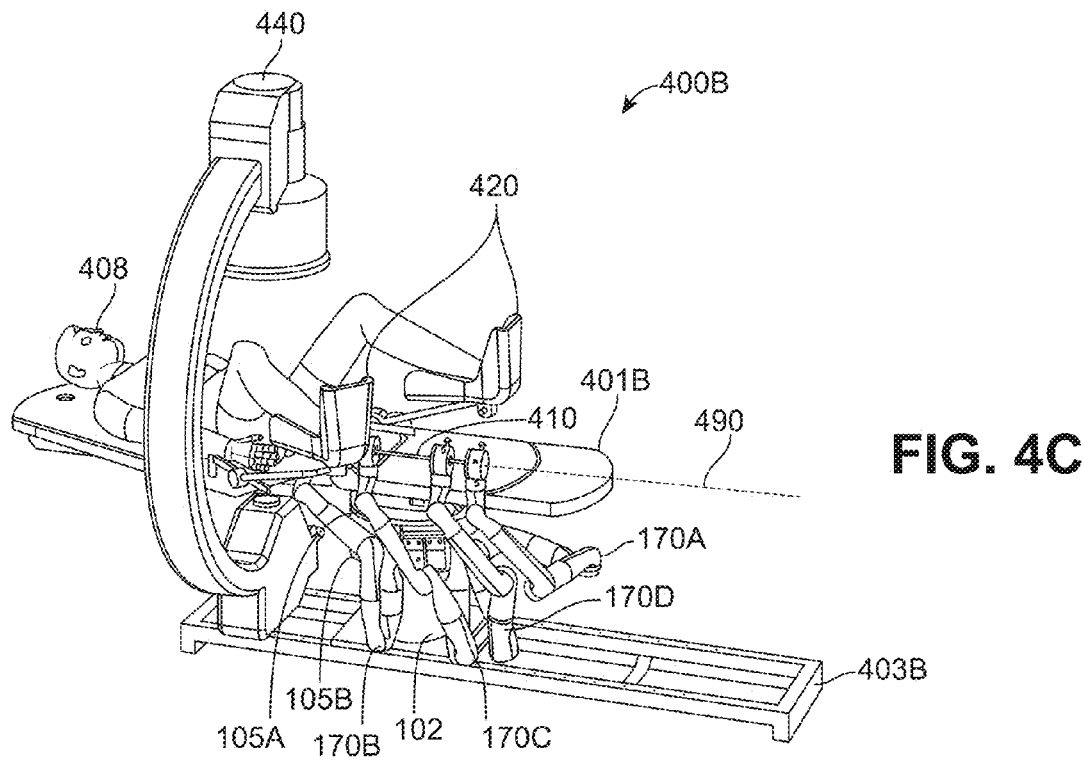
FIG. 4C is a perspective view of an imaging device and a surgical robotics system with column-mounted arms configured to access the lower body area of a patient according to one embodiment.

FIG. 4C is a perspective view of an imaging device 440 and a surgical robotics system 400B with column-mounted arms configured to access the lower body area of a patient 408 according to one embodiment. The surgical robotics system 400B includes a pair of stirrups 420 that support the legs of the patient 408 in order to expose the groin area of the patient 408. Generally, the imaging device 440 captures images of body parts or other objects inside a patient 408. The imaging device 440 may be a C-arm, also referred to as a mobile C-arm, which is often used for fluoroscopy type surgical procedures, or another type of imaging device. A C-arm includes a generator, detector, and imaging system (not shown). The generator is coupled to the bottom end of the C-arm and faces upward toward the patient 408. The detector is coupled to the top end of the C-arm and faces downward toward the patient 408. The generator emits X-ray waves toward the patient 408. The X-ray waves penetrate the patient 408 and are received by the detector. Based on the received X-ray waves, the imaging system 440 generates the images of body parts or other objects inside the patient 408. The swivel segment 210 of the table 119 is rotated laterally such that the groin area of the patient 408 is aligned in between the generator and detector of the C-arm imaging device 440. The C-arm is a physically large device with a footprint stationed underneath the patient during use. In particular, the generator of the C-arm is disposed underneath the operative area of the patient, e.g., the abdomen area. In typical surgical beds mounted to a column, the column interferes with the positioning of the C-arm generator, e.g., because the column is also underneath the operative area. In contrast, due to the configurability of the swivel segment 210, the surgical robotics system 400B may configure the table 119 such that the C-arm, the robotic arms, and a user (e.g., physician) have a sufficient range of access to perform a surgical procedure on a working area the patient's body. In one example use case, the table 119 is translated laterally along a longitudinal axis of the table 119 such that the robotic arms can access the groin or lower abdomen area of a patient on the table 119. In another example use case, by rotating the swivel segment 210 away from the column 121, the generator of the C-arm 440 may be positioned underneath the groin area of the patient 408. The swivel segment 210—with a patient lying on the swivel segment 210—may be rotated at least to 15 degrees relative to a longitudinal axis of the table 119 without tipping over the surgical robotics system. In particular, the surgical robotics system does not tip because the center of mass of the surgical robotics system (e.g., the center of mass of the combined, at least, table, bed, and base) is positioned above a footprint of the base.

The surgical robotics system 400B uses a set of column-mounted robotic arms to manipulate a surgical instrument 410. Each of the robotic arms is coupled to, e.g., holding, the surgical instrument 410. The surgical robotics system 400B uses the robotic arms to insert the surgical instrument 410 into the groin area of the patient along a virtual rail 490.

Figure 4D:
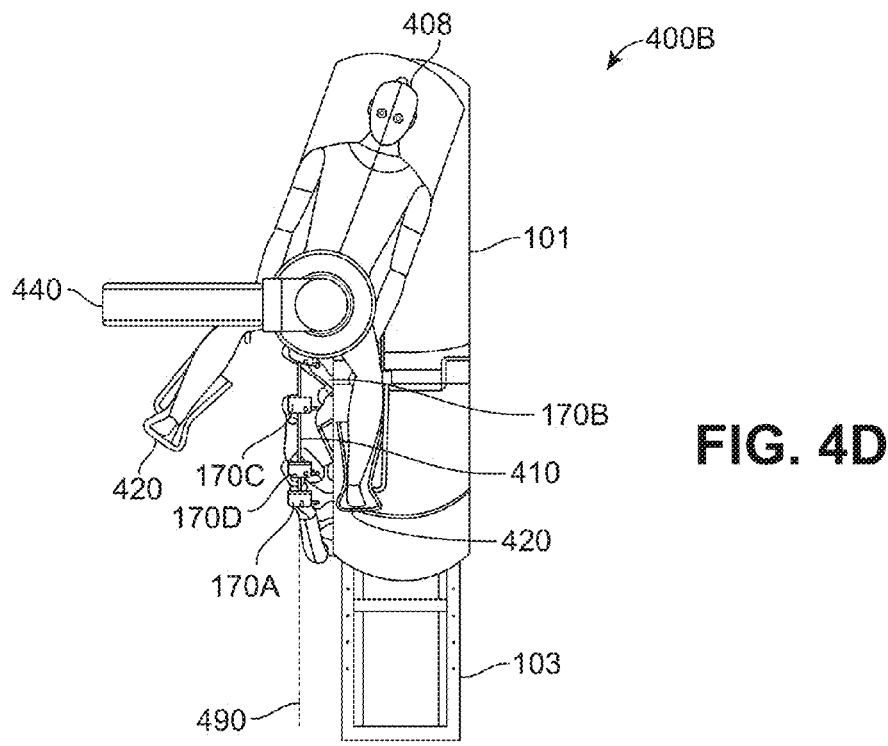
FIG. 4D is a top view of the imaging device and the surgical robotics system with column-mounted arms configured to access the lower body area of the patient according to one embodiment.

FIG. 4D is a top view of the imaging device 440 and the surgical robotics system 400B with column-mounted arms configured to access the lower body area of the patient 408 according to one embodiment.

III. Basket Apparatus

Figure 5A:
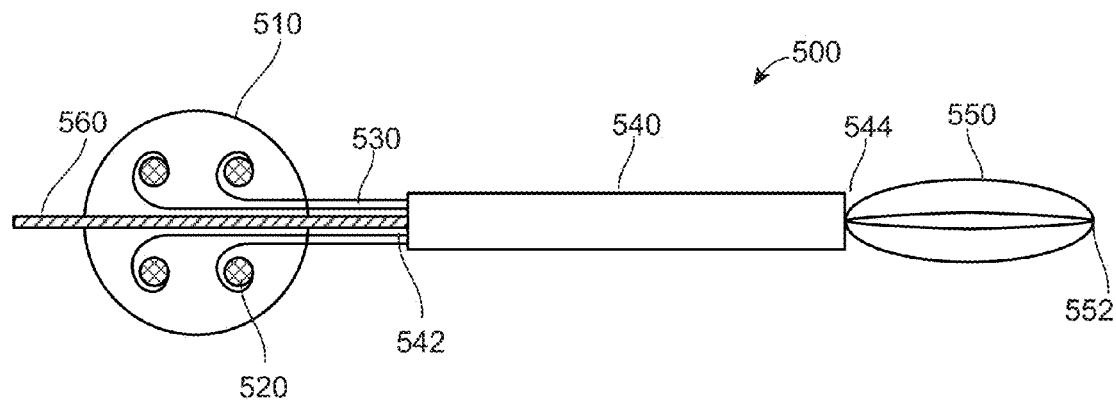
FIG. 5A is a side view of a basket apparatus according to one embodiment.
Figure 5B:
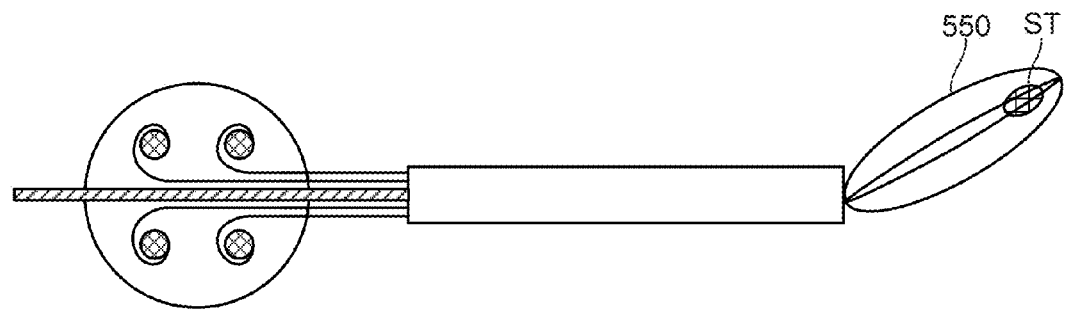
FIGS. 5B and 5C illustrate how the basket apparatus may be used to capture a kidney stone according to one embodiment.
Figure 5C:
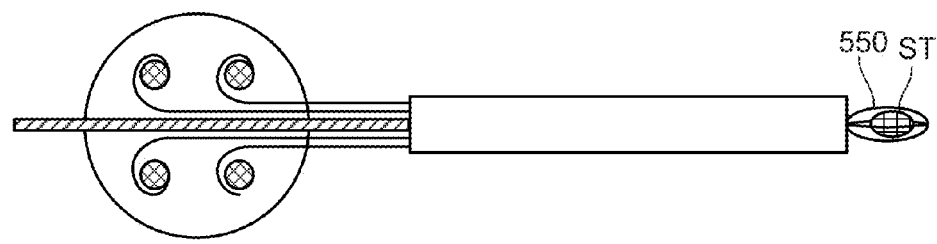

Referring now to FIGS. 5A to 5F, a robotically steerable basket apparatus is described. FIG. 5A is a side view of the basket apparatus. FIGS. 5B and 5C illustrate how the basket apparatus may be used to capture an object, such as a urinary stone, according to one embodiment. The robotically steerable basket apparatus 500 may be operatively and removably coupled to any of the IDMs described herein and above, such as IDM 117 described above. The robotically steerable basket apparatus 500 may be advanced through a natural or artificially created orifice in a subject or patient to capture a target object within the body of the subject or patient. For instance, the robotically steerable basket apparatus 500 may be advanced with the robotic surgical system 100 through the urethra, and optionally the bladder, ureter, and/or the kidney to capture a kidney stone (ST). As another example, the robotically steerable basket apparatus 500 may be advanced into the gallbladder to capture a gallstone. In some embodiments, the robotically steerable basket apparatus 500 may be advanced through another working channel of a catheter, ureteroscope, endoscope, or similar device (e.g., within a 1.2 mm diameter working channel). In those embodiments, the addition of an endoscopic instrument may provide axial support and stiffness, while also delivering additional features, such as vision, navigation, and localization capabilities, to the apparatus.

The robotically steerable basket apparatus 500 may include a handle or tool base 510 adapted to removably and operatively couple with the IDM 117. The tool base 510 may include a number of capstans 520 to couple to the output shafts or drive units of the IDM so that the IDM can actuate the capstans 520 as well as other actuation elements coupled thereto. The basket apparatus 500 further includes a number of pull wires (also referred to as tendons) 530. The pull wires 530 are coupled to the capstans 520 at one end. The pull wires 530 run straight along the long axis of the apparatus 500, and are prevented from sagging or twisting by an outer support shaft 540. The outer support shaft 540 may include a plurality of lumens and channels through which the pull wires 530 may traverse along the direction of the long axis of the apparatus 500. The outer support shaft 540 may be flexible to facilitate advancement of the basket apparatus 500 through a tortuous tissue tract or bodily channel, such as the urethra and ureter. The apparatus 500 may also include an internal shaft 560 for axial stiffness and support. The apparatus 500 may be configured to be inserted into the working channel of an instrument such as an endoscope 118.

The pull wires 530 may be coupled to one another at the distal-most tip 552 of the basket apparatus 500. For example, the basket apparatus 500 may include two different pairs of pull wires 530, with each pull wire pair forming a loop with the tips of the loops coupled to one another at tip 552 and each pull wire having its two ends threaded through opposite peripheral channels or lumens 548 of the outer support shaft 540. The two tips of the looped pull wires may be coupled together in any number of ways. For example, they may be soldered together, crimped together, braided together, bonded together with an adhesive, tied together with a suture or other thread, etc. Once connected together, each pair of pull wires forming a loop can also be referred to as a single pull wire, if that terminology is preferred in a particular implementation.

When the tool base 510 is coupled to an IDM, the capstans 520 may actuate the pull wires 530 so that the pull wires 530 can be translated proximally or distally in the axial (long axis) direction, such as relative to the outer support shaft 540. One or more of the pull wire 530 may be translated independently from one another, such as by their respective capstans 520.

The distal ends of the pull wires 530 may extend from the distal end 544 of the outer support shaft 540 to form a distal wire basket 550. The distal ends of the pull wires 530 may be retracted by the capstans 520 located at the proximal end 542 of the outer support shaft 540 to collapse the basket 550 into the outer support shaft 540. Retraction of the basket 550 into the outer support shaft 540 can lower the profile of the basket apparatus 500 to facilitate the advancement of the basket apparatus 500 into a tissue tract or bodily channel. In some embodiments, the apparatus 500 may be deployed through a working channel of an endoscopic device, wherein the apparatus 500 may be retracted relative to the endoscopic device in order to similarly lower the profile of the basket apparatus 500. Conversely, the capstans 520 may be actuated to extend the pull wires 530 out from the outer support shaft 540 so that the basket 550 may expand. For instance, once the distal end 544 of the outer support shaft 540 is positioned near a stone ST, the basket 550 may be expanded to capture the stone ST.

The basket 550 may be extended from outer support shaft 540 at different amounts of extension to vary the size of the basket 550. For instance, as illustrated in FIGS. 5B and 5C, the basket 550 may initially be extended to an enlarged size to capture the stone ST within the basket 550 and then the basket 550 may be partially collapsed (i.e., reduced in size) to secure the stone within the basket 550. As further shown in FIG. 5B, the pull wires 530 may be selectively actuated to steer or tip the basket 550 to facilitate capture of the stone ST. The outer support shaft 540 may be held stationary relative to the pull wires 530 while the pull wires 530 are differentially actuated. The basket 550 may be steered in any number of directions by the differential actuation of the individual pull wires 530 such that it has a 360° range of motion. For example, one end of an individual pull wire 530 may be held stationary while the other end is pulled or pushed to tip the basket 550 toward or away from the moving end, respectively. In other examples, the individual ends of the pull wires 530 may be differentially pulled, pushed, or held stationary to vary the degree and/or direction of the tipping.

The degree of movement of the capstans 520 may be indicative of the degree and/or direction of the tipping of the basket 550 and also of its current size. Therefore, in some embodiments, the robotic system, and the IDM in particular, can determine and/or track the current configuration of the basket 550 positioned within a subject or patient's body based on the feedback or information from the capstans 520, the drive unit(s), or output shaft(s) and without visualization of the basket 550. Alternatively or in combination, the basket 550 may be visualized to determine and/or track its current configuration. The pull wires 530 may be formed from a shape memory material or metal (e.g., a Nickel-Titanium alloy such as Nitinol) so that the distal ends of the pull wires 530 may be biased to assume the basket shape when unconstrained and/or at body temperature.

Figure 5D:
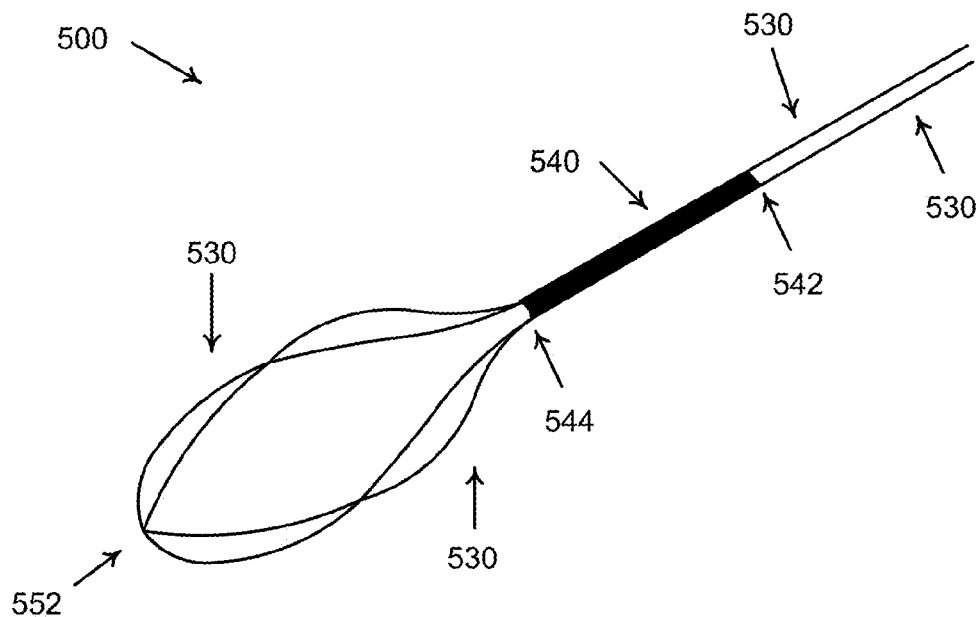
FIG. 5D shows a perspective view of the robotically steerable basket apparatus, according to one embodiment.
Figure 5E:
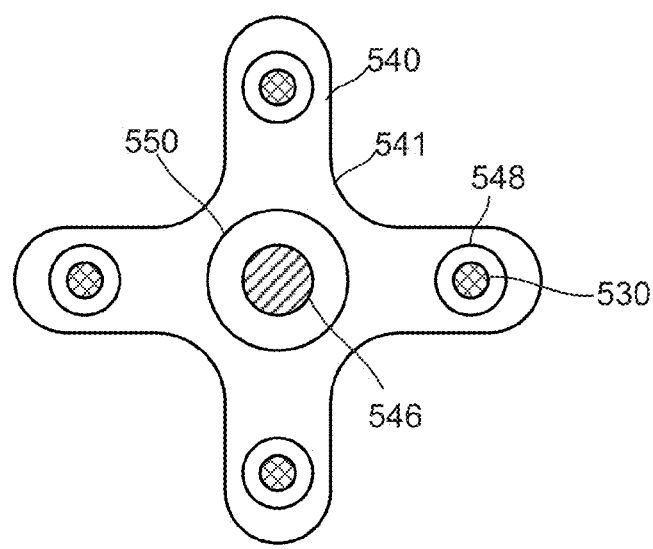
FIG. 5E shows a planar view of the robotically steerable basket apparatus along the plane perpendicular to the center axis of the outer support shaft, assuming it is straight, according to one embodiment.
Figure 5F:
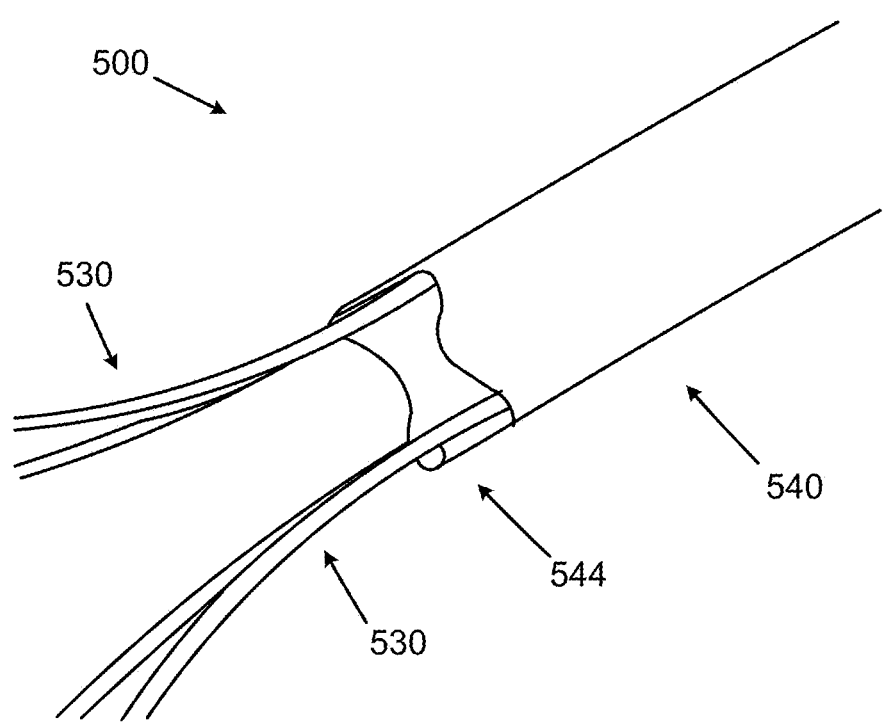
FIG. 5F and illustrates a close up view of the distal end of the outer support shaft of the basket apparatus, according to one embodiment.

FIGS. 5D, 5E, 5F illustrate different views of an embodiment that is intended for use within the working channel of an endoscopic device. FIG. 5D illustrates a perspective view of the outer support shaft of the basket apparatus, while FIG. 5E illustrates a close up side view of the outer support shaft. As shown in FIG. 5E, the outer support shaft 540 may have a square or diamond shaped cross-section. Other shapes such as a circle, ellipse, oval, triangle, quadrilateral, rectangle, pentagon, star, hexagon, and other polygonal shapes for the cross-section of the outer support shaft 540 are also contemplated. The outer support shaft 540 may include a central working channel 546 and a plurality of peripheral channels 548. The pull wires 530 may be positioned within the peripheral channels 548. A guide wire, a further therapeutic device (such as a laser fiber for lithotripsy), or a diagnostic device (such as an imaging device or a camera) may be advanced through the central channel 546 to reach a target area or object, such as a captured stone ST.

The outer support shaft 540 may also comprise a plurality of rounded vertices or corners 543 where the peripheral channels 548 are located and through which the pull wires 530 travel. Slotted lateral edges 541 on the outer surface of the outer support shaft 540 may be concave, and thus at least partially curved around the corners 543 where the peripheral channels 548 are located so as to define a plurality of elongate lateral slots or channels of the outer support shaft 540. These slotted lateral edges 541 may facilitate advancement of the basket apparatus 500 by discouraging apposition of tissue to the edges of the outer support shaft. When the basket apparatus 500 is positioned through a tissue tract, bodily channel, or the working channel of an endoscopic device, the slotted lateral edges 541 may provide sufficient space to allow fluid irrigation and/or aspiration between the outer support shaft 540 and the inner walls of the tissue tract, bodily channel, or working channel.

FIG. 5F shows a perspective view of a robotically steerable basket apparatus, such as the device in FIG. 5D, zoomed in to illustrate the distal end 544 of the outer support shaft 540 with the pull wires exiting the peripheral channels 548 according to one embodiment.

Figure 6A:
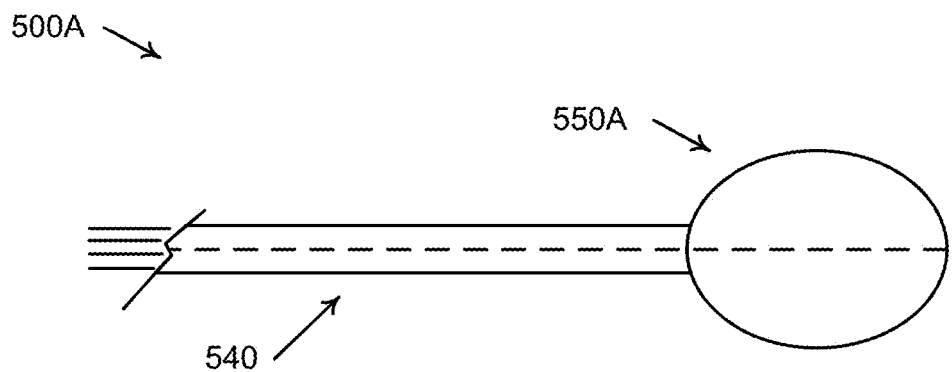
FIG. 6A illustrates an embodiment where the basket has have a spherical shape.
Figure 6B:
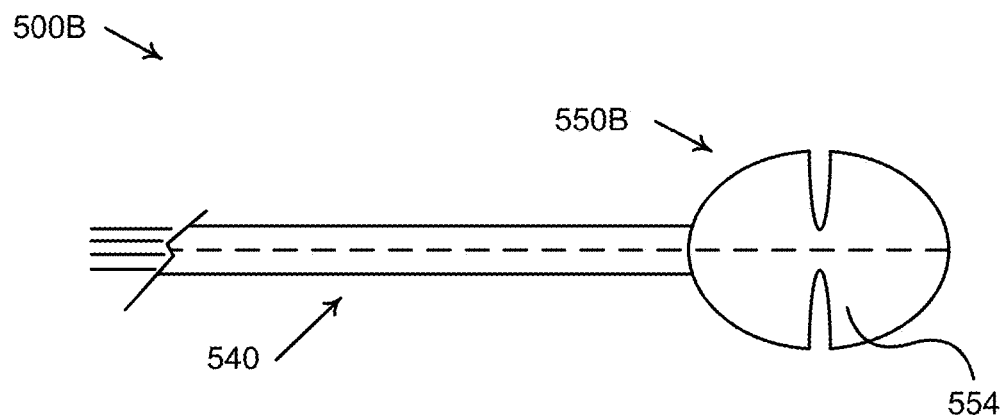
FIG. 6B illustrates an embodiment where the basket is shaped so as to form jaws.
Figure 6C:
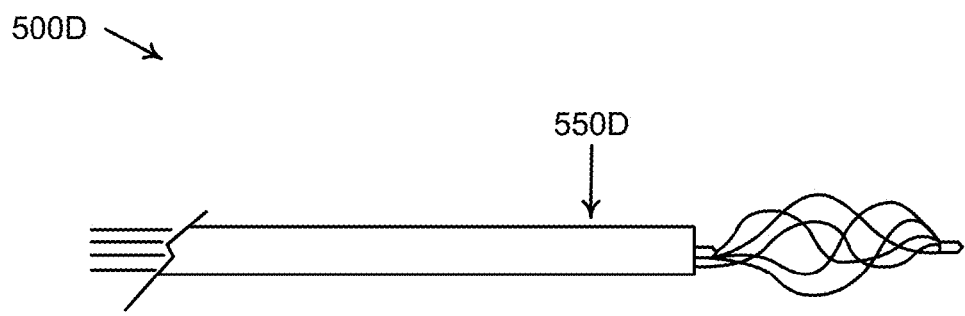
FIG. 6C illustrates an embodiment where the basket is formed of spiral or helically shaped pull wires.

FIGS. 6A-6C show example shapes for the expanded basket, according to one embodiment. When the basket 550 is expanded (e.g., not entirely collapsed with the outer support shaft 540, or extended past the distal end of an endoscopic device), it may have any number of shapes, such as an elliptical shape as shown in FIG. 5A. As an alternative, FIG. 6A illustrates an embodiment where the basket 550B has have a spherical shape. As another alternative, FIG. 6B illustrates an embodiment where the basket 550B is shaped to have the pull wires have a semi- or fully rigid indentation 554 so as to form the shape of "jaws" for improved reaching capabilities within tortuous anatomy. As another alternative, FIG. 6C illustrates an embodiment where the basket 550C is formed of spiral or helically shaped pull wires for alternative reaching capabilities within tortuous anatomy.

FIGS. 7A-7E illustrate various techniques for using the basket apparatus to break up a captured stone, according to one embodiment. The captured stone may be broken apart in many ways.

Figure 7A:
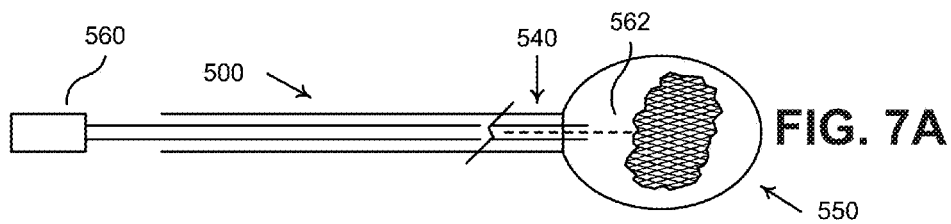
FIG. 7A illustrates insertion of a laser or optical fiber to break up a captured stone, according to one embodiment.

FIG. 7A illustrates insertion of a laser or optical fiber to break up a captured stone, according to one embodiment. The captured stone ST may be broken apart with laser or optical energy, referred to as laser lithotripsy. In such a use case, a laser or optical fiber 562 is introduced from the tool base or handle 510 and advanced through the central working channel 546 so that a laser tip or optical element is positioned at the proximal end of the basket 550. The central working channel 546 may have an appropriate size to accommodate the laser or optical fiber, such as 100-300 μm in diameter. The laser or optical fiber may convey laser or light energy to be directed by the laser tip or optical element to break apart the captured stone ST. Alternatively or in combination, a fluid may be flushed through or aspirated through the central working channel 546. Alternatively, a fluid may be flushed through or aspirated through slotted lateral edges 541 as discussed with respect to FIG. 5E.

The captured stone ST may be broken apart mechanically in many ways as well. For example, ultrasound may be applied such as through the central channel 546 (not shown). Alternatively or in combination, a mechanical device may be advanced through the central channel 546 and the mechanical device may be used to break apart the captured stone.

Figure 7B:
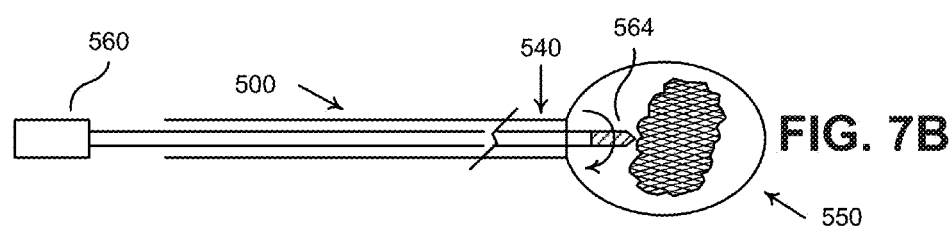
FIG. 7B illustrates insertion of a mechanical drill to break up a captured stone, according to one embodiment.

FIG. 7B illustrates insertion of a mechanical drill to break up a captured stone, according to one embodiment. The mechanical drill bit 564 is advanced through the central working channel 546 of the outer support shaft 540. A rotating motor, located proximal to the tool base 510, rotates the drill bit 564 at the basket 550 to break apart the captured stone ST.

Figure 7C:
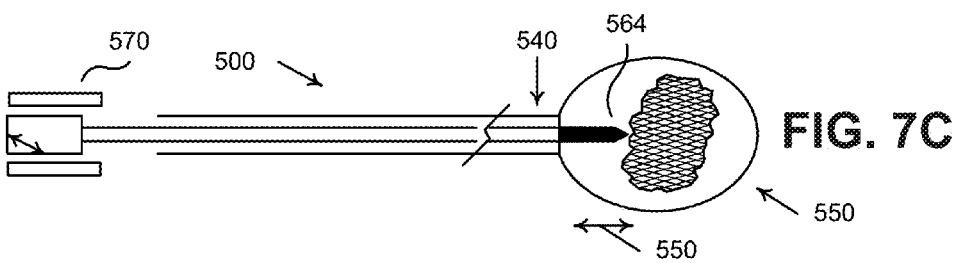
FIGS. 7C and 7D illustrate use of a chisel to break up a captured stone, according to one embodiment.
Figure 7D:
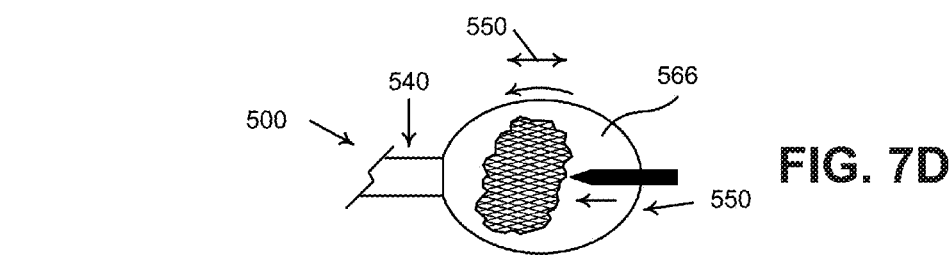

FIGS. 7C and 7D illustrate use of a chisel to break up a captured stone, according to one embodiment. In the embodiment of FIG. 7C, the chisel 566 is advanced through the central working channel 546 of the outer support shaft 540. The chisel 566 is actuated with a reciprocating motor (not shown) located proximal to the tool base 510. The reciprocating motor may drive the chisel 566 axially in the proximal and distal directions. In the embodiment of FIG. 7D, the chisel 566 is provided from a device separate from the apparatus 500, and thus is not advanced through the basket apparatus 500, to break apart the captured stone ST from another direction such as the distal direction. In this case, the working channel 546 of the basket apparatus 500 may be used to evacuate stone fragments.

Figure 7E:
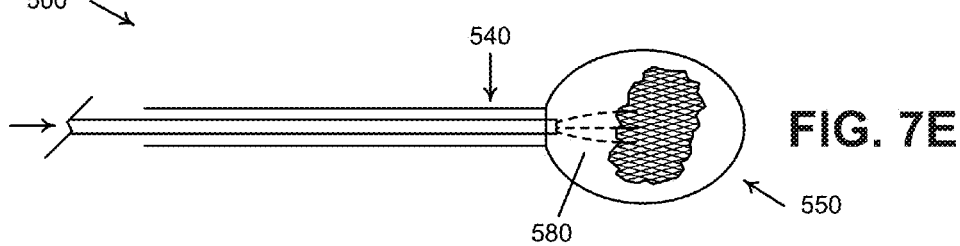
FIG. 7E illustrate use of a high pressure fluid jet to break up a captured stone, according to one embodiment.

FIG. 7E illustrate use of a high pressure fluid jet 580 to break up a captured stone, according to one embodiment. The high pressure fluid jet 5280 may be water, saline, or another liquid ejected from a fluid source. The fluid jet may be abrasive and comprise particulates such as salt particles to facilitate stone destruction. An example implementation may have a pressure of 400 psi and a 100 μm diameter on the central working channel 546 from which the fluid jet exits towards the stone ST.

The captured stone ST may be steered by the basket 550 while the captured stone ST is being broken apart. Once the captured stone ST is broken apart in any of the ways described, the broken apart stone ST may be aspirated through the central channel 546 and/or the broken apart stone ST may be secured by the basket 550 (such as in a lower profile than if the whole stone ST were secured) to be retracted from the target site (e.g., ureter, renal pelvis, gallbladder, etc.). In some embodiments, the broken apart portions of the captured stone ST may be aspirated while the basket 550 continues to capture and secure the larger portions of the captured stone ST that have not yet been broken apart.

IV. Process for Capturing Stones in a Basket Apparatus

IV.A. Problem

Basketing is a technique frequently used by urologists to remove urinary stones or stone fragments from the urinary tract. The current state of the art generally requires at least two experienced operator to control the ureteroscope and the basket apparatus in tandem. Procedure time and clinical outcome can be negatively impacted if one or more of the operators lack sufficient experience.

Current procedure for removing urinary stones involves advancing a ureteroscope into the ureter via the urethra and bladder. The ureteroscope is positioned approximately close to a urinary stone. During a basketing phase of the operation, a basket is advanced through the ureteroscope and may capture the urinary stone with its basket to extract the stone. With the ureteroscope positioned at the stone, the urologist has several potential workflow options for moving the stone. If the stone is small enough that the operator is able to capture the entire stone in the basket, then both the ureteroscope and the basket are withdrawn back to the bladder or outside the subject. If the stone is too big to withdraw in one pass, a laser (Holmium or neodymium-doped yttrium aluminum garnet (ND:YAG)) or a electrohydraulic lithotripsy (EHL) device can be passed through a central working channel of the ureteroscope and used to fragment the stone into smaller pieces. One operator can then exchange the laser fiber or EHL probe for the basket and can extract each stone fragment in turn to the bladder or outside the patient. If the stone is located in the proximal (relative to the center of the body of the subject) ureter or inside the kidney itself, a sheath can be used to enable rapid extraction and introduction of the ureteroscope and the basket.

Such a procedure requires two operators. The primary operator controls the ureteroscope and the secondary operator controls the basket or any other inserted tools such as the laser. Both the primary operator and the secondary operator can be looking at a visual feed from a ureteroscope camera.

Figure 8A:
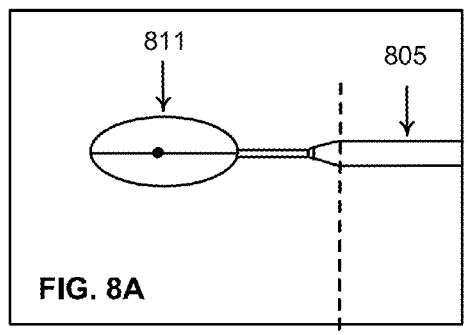
FIGS. 8A-8C illustrate a significant challenge that can face operators during a basketing operation, according to one embodiment.
Figure 8D:
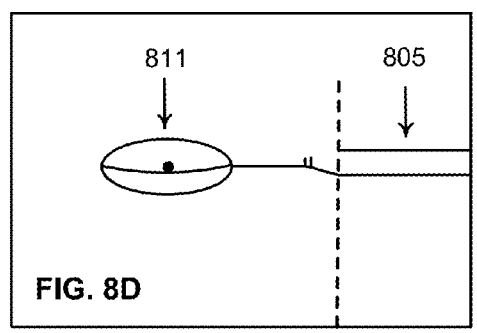
FIGS. 8D-8F illustrate a process for overcoming the challenge in basketing a stone, according to one embodiment.
Figure 8B:
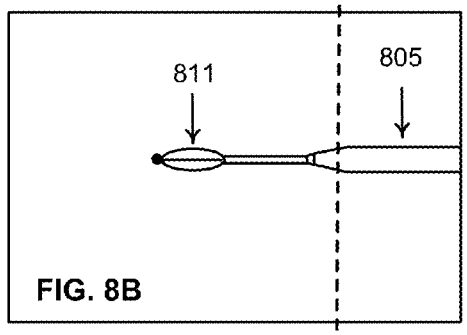
Figure 8E:
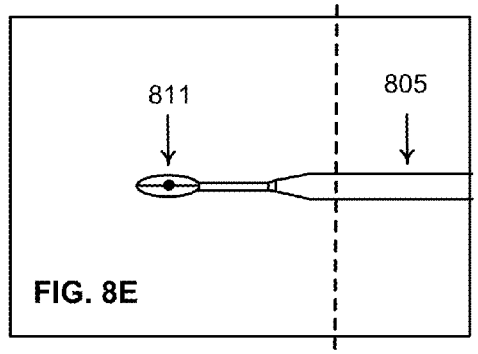
Figure 8C:
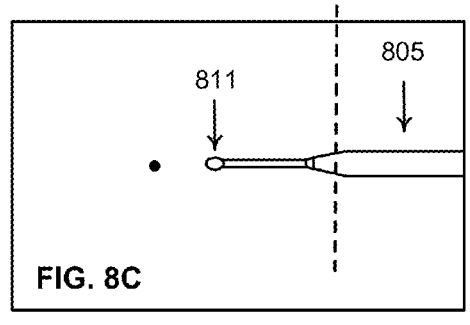

FIGS. 8A-8C illustrate a significant challenge that can face operators during a basketing operation, according tone one embodiment. In FIG. 8A, assume that the operator has advanced through the basketing phase to the point where the stone ST is now located within the open (i.e., unclosed or un-retracted) basket 802, by navigation of the basket, where the basket has been advanced out of the ureteroscope 805. Despite being located around the stone ST prior to retraction, retracting the basket 802 so that the stone ST is trapped in the basket 802 when the basket 802 is retracted is a significant challenge. This can be difficult because the center 811 of the basket 802 can retract laterally along the long axis of the basket as the operator closes the basket 802. In this scenario, if the operator initially positions the basket 802 center 811 over the stone ST (FIG. 8A) and closes or collapses the basket 802 (FIG. 8B), the basket 802 frequently retracts past the stone ST (see moved center 811 of the basket 802) and fails to trap it (FIG. 8C).

IV.B. Manual Process

Figure 8F:
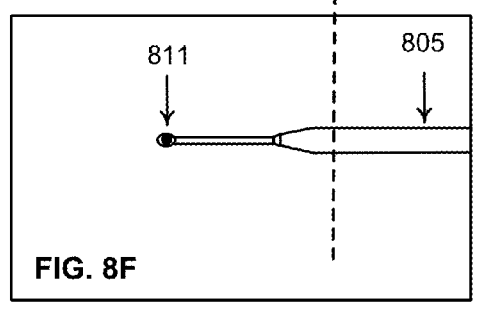

FIGS. 8D-8F illustrate a process for overcoming the challenge in basketing a stone, according to one embodiment. In this process, two operators work together to advance the ureteroscope 805 and/or the basket 802 in tandem as the basket 802 is closed to ensure the stone ST is trapped. FIG. 8D shows the basket 802 expanded and positioned to enclose the stone ST. FIG. 8E shows the basket 802 being collapsed while either the ureteroscope 805 or the basket apparatus (not explicitly shown, enclosed by the ureteroscope 805) is advanced, thereby holding the center 811 position of the basket in place relative to the stone ST. The ureteroscope 805 or basket apparatus may be moved relative to the pull wires through motion of either instrument as a whole by the operator. FIG. 8F shows the stone ST securely captured or trapped by the basket 802. After capture, the stone may be extracted from the patient by retracting the basket and/or the ureteroscope from the patient.

While the procedure above allows a stone ST to be more reliably captured, such a procedure typically requires two or more well trained operators who must work together with a high degree of coordination. For example, a first operator may be tasked with collapsing the basket with a first controller while a second operator may be tasked with advancing the basket apparatus with a second controller.

IV.C. Robotic Process

Robotic control can simplify the basketing phase operation, thus reducing the complexity of the procedure, the time to perform it. Robotic control also removes the need for more than one operator to be present to coordinate and accomplish the basketing phase.

FIGS. 9A-9F illustrate a process for positioning and controlling a basket apparatus to trap stones (and stone fragments) during a robotically assisted ureteroscopy intervention, according to one embodiment. The surgical robotics system 100 includes a robotically controllable ureteroscope 805 which itself includes a sheath component 815, a leader component (or leaderscope) 825, and a basket 802. Throughout the process, aspiration and irrigation/fluid transfer may be performed through the space between the leader and sheath through port 835, and/or they may be performed through the working channel of the ureteroscope, and through the slotted edges of an inserted basketing apparatus as described with respect to FIG. 5E above.

The system further includes at least two robotic arms 102A and 102B which are configured to control the position, orientation and tip articulation of the sheath 815 and leader 825, through instrument bases 801A and 801B for the sheath 815 and leader 825 respectively. In this example, at least one additional robotic arm 102C having a tool base 102C is configured to control the position and basket actuation of the basket 802. The system 100 may further include a graphical user interface suitable for controlling the ureteroscope 805 and basket 802, and a control system suitable for taking command inputs from the user interface and servoing the appropriate motor of the appropriate arm 102. The arms 102A-C, particularly their bases 801A-C, may be aligned in a virtual rail configuration.

Figure 9A:
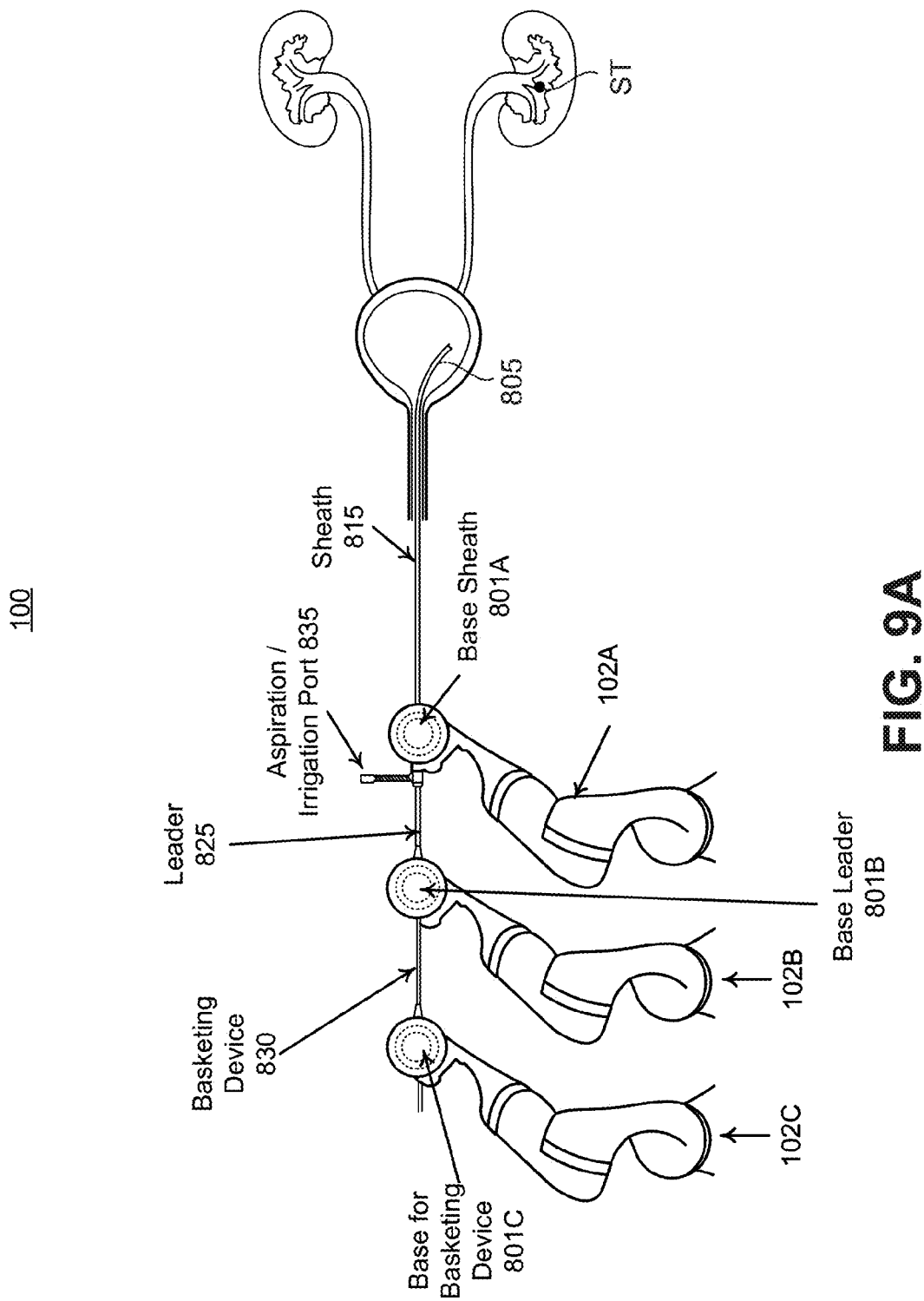
FIGS. 9A-9F illustrate a process for positioning and controlling a basket apparatus to trap stones (and stone fragments) during a robotically assisted ureteroscopy, according to one embodiment.
Figure 9B:
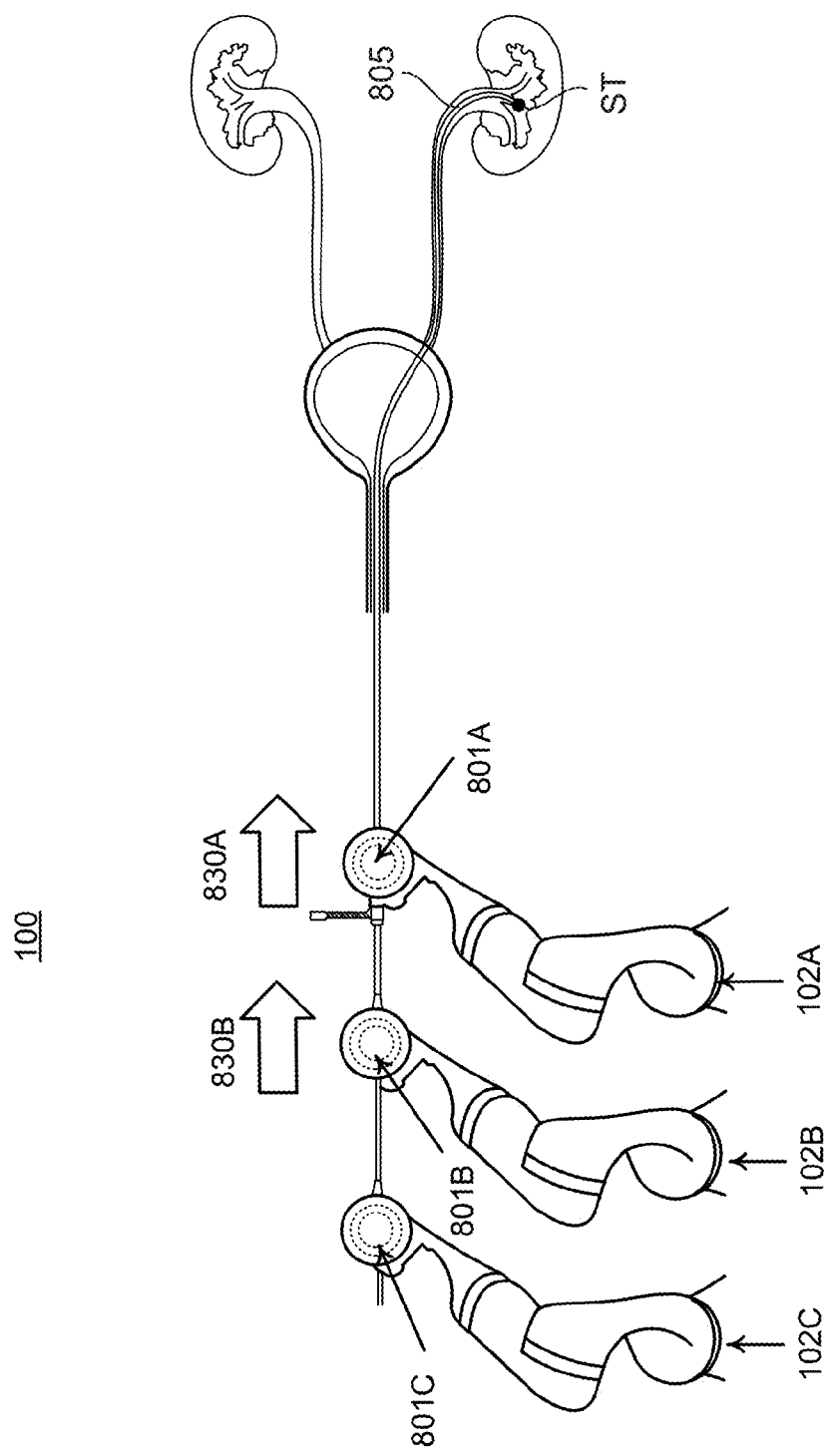
Figure 9C:
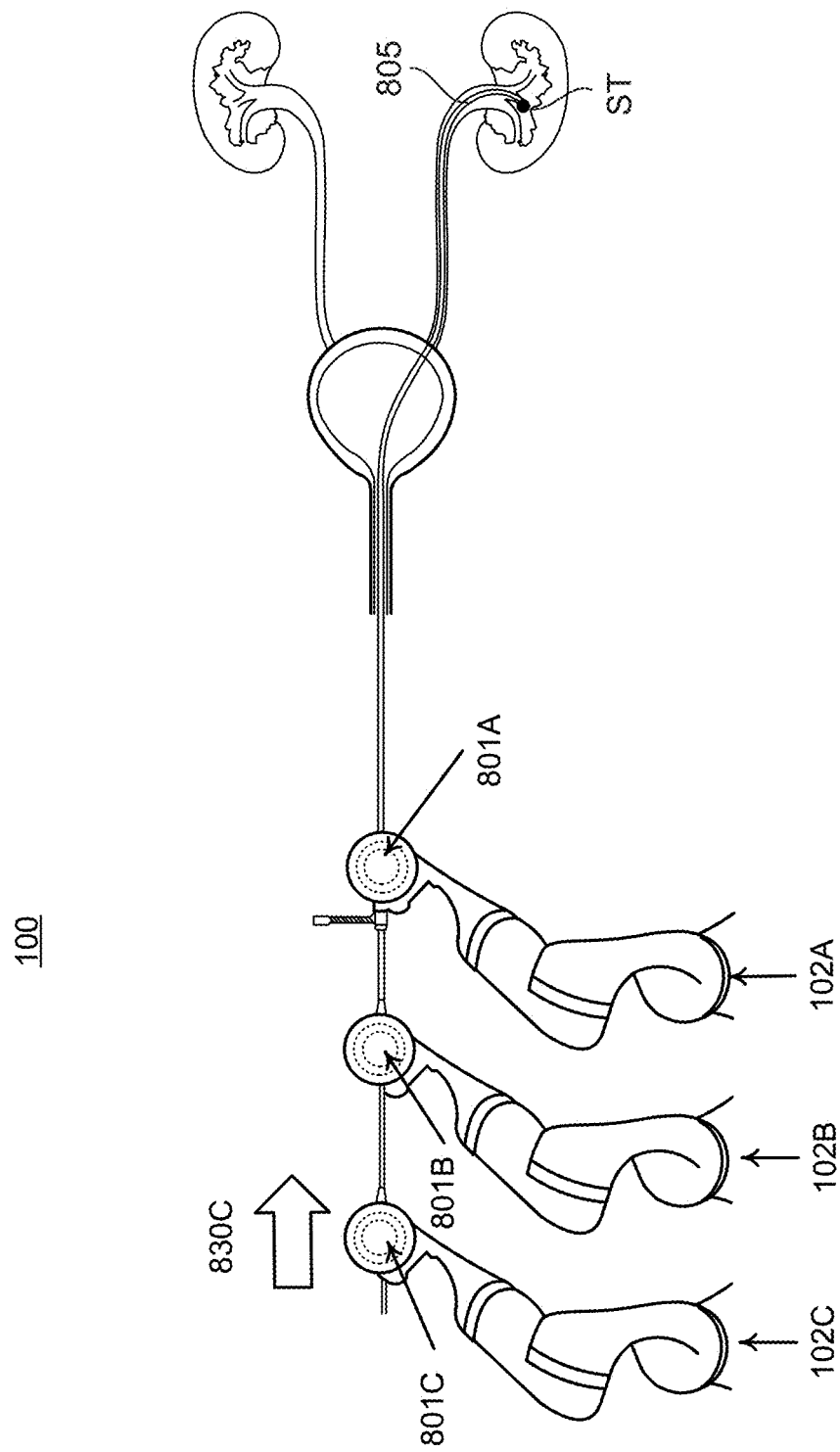

To carry out the process of the operation, the system 100 steers the robotic ureteroscope 805 (for example, either automatically or using operator input received via controls and displayed via the GUI) into position such that the stone ST can be visualized using a tip mounted camera (not shown) in the ureteroscope 805. As shown in FIG. 9B, the first 101A and second 101B instrument bases advance the sheath 815 and the leader 825, respectively, of the ureteroscope 805 relative to the patient in the directions indicated by a first arrow 830A and a second arrow 830B, respectively. The speed and magnitude of the motions of the sheath 815 and leader 825 may vary from each other, and the two parts may move independently from each other. The ureteroscope 805 is advanced through the bladder BL and the ureter UTR. As shown in FIG. 9C, the tool base 801C advances the basket 802 out of the working channel of the ureteroscope 805 in the direction indicated by a third arrow 830C. In one specific implementation of this process, an introducer, such as a rigid metal cystoscope, may be used to help insert the ureteroscope (sheath, leader, or both) into the patient's urethra.

Figure 9D:
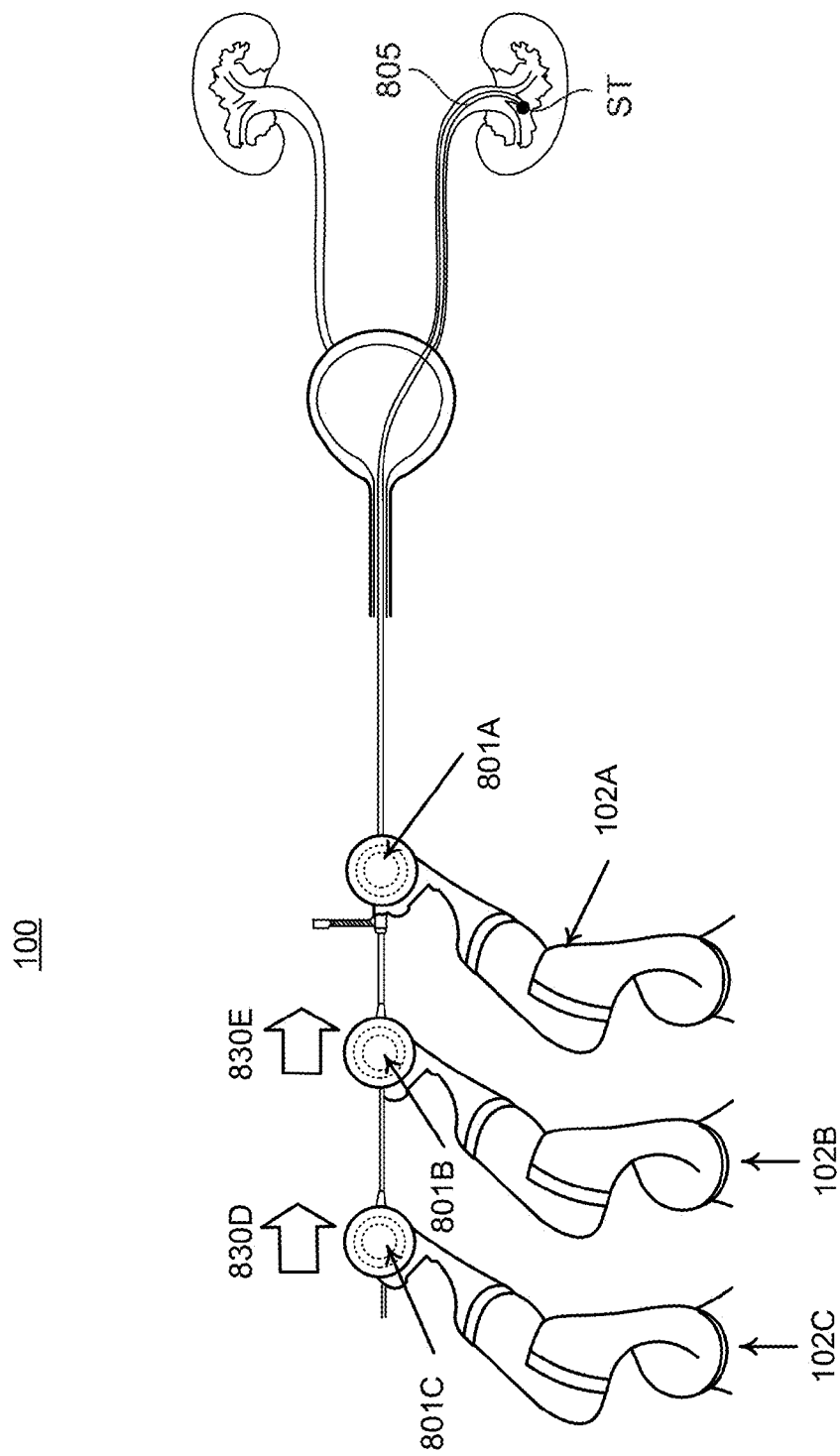

As shown in FIG. 9D, the system commands the basket 802 to open and positions the basket 802 such that the stone ST is located in the center of the basket 802. This may be accomplished, as shown by the fourth arrow 830D, by advancing one or more of the pull wires of the basket 802 using the tool base 801C, or using another arm/tool base (not shown) that separately controls the pull wires from the remainder of the basket apparatus. This may also be in part accomplished, as shown by the fifth arrow 830E, by advancing the leader 825 using the second instrument base 801B, which in turn repositions the basket 802 advanced out of the leader 825.

Figure 9E:
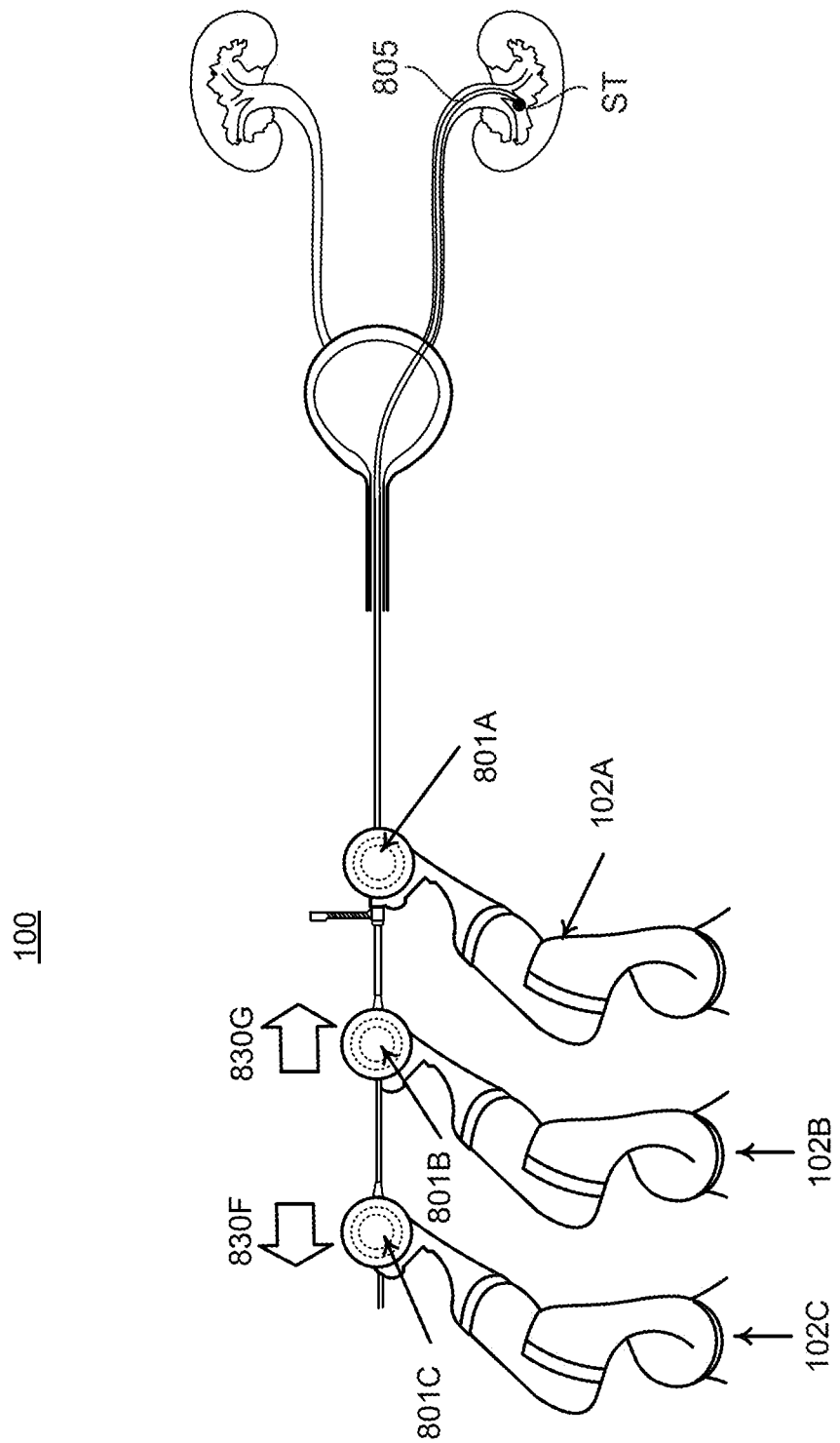

As shown in FIG. 9E, the system then commands the basket 802 to close. This may be accomplished, as shown by the sixth arrow 830F, by retracting the pull wires of the basket 802, again using the tool base 801C or using another arm/tool base (not shown) that separately controls the pull wires from the remainder of the basket apparatus. As the basket 802 closes, either the leader's 825 instrument base 801B or the basket apparatuses' tool base (not shown) may also simultaneously advance the leader 825 or the basket 802, respectively, in the direction indicated by seventh arrow 830G to maintain the stone ST in the center of the basket 802 while the basket is being closed until the stone ST is trapped.

Figure 9F:
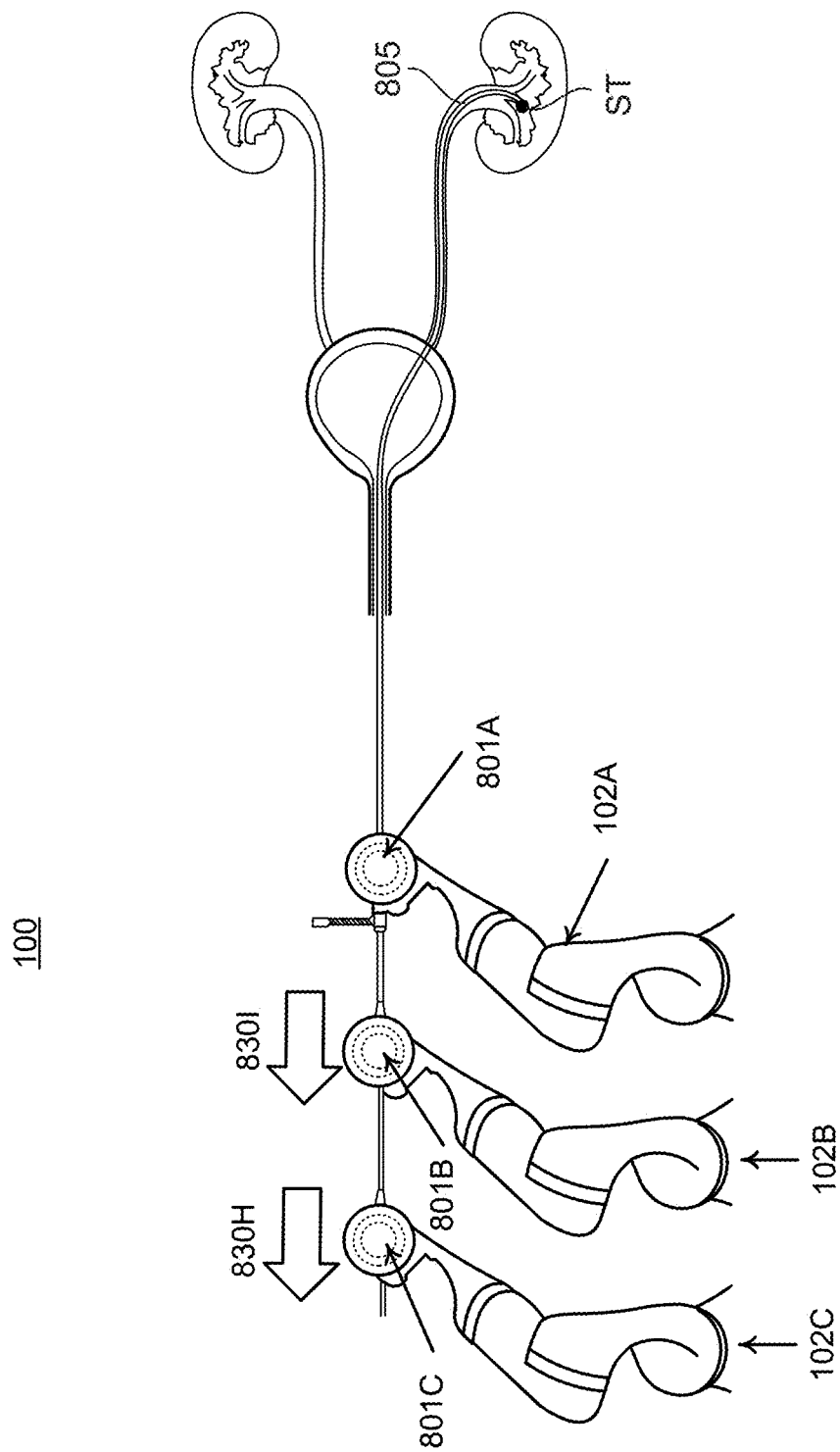

As shown in FIG. 9F, once the stone ST is trapped, the system removes or retracts the basket apparatus 802 and leader 825, according to the eighth 830H and ninth 830I arrows using the tool base 801C and instrument base 801B, respectively, from the subject so the stone ST can be fully extracted from the patient.

V. Process for Percutaneous Nephrolithotomy

V.A. Problem

Some ureteral stones are sufficiently large that removal via ureteroscope is impractical. For example, stones can be greater than 2 centimeters in diameter, and generally the working channel of a ureteroscope through which a stone or fragment can be removed has a diameter of 1.2 millimeters. Although breaking stones into smaller fragments for removal via ureteroscopy does work in many instances, studies have shown that leftover stone debris is often the source of new stone formation, necessitating future similar treatments.

Percutaneous nephrolithotomy (PCNL), in contrast, is a process for stone removal whereby a surgeon cuts into the kidney from outside the body (rather than entering through the ureter) to provide a larger port for stone removal. As no ureteroscope is used to identify the location of the stone within a kidney, the location of the stone must be identified by other mechanisms. A common technique is to use traditional imaging techniques, such as a X-ray computed tomography (CT) scan or fluoroscopy using an intravenous pyelogram, to identify the location of the stone.

Having collected this information it is common for a urologist, who is trained to remove the stone, to ask a radiologist to perform the percutaneous cut to place a guide wire leading near the location of the stone in the kidney out through the cut and outside the body. The cut may be obtained by directing a nephrostomy needle into the patient's body, the nephrostomy needle comprising of a stylet and a cannula. Having directed the needle into the patient, the stylet may be removed, leaving the cannula to form an open port to the location of the kidney stone. Through the cannula, the urologist may then place the guide wire. The urologist can then use this wire to perform the remainder of the PCNL process to remove the stone. It is common for a urologist to ask a radiologist to place the guide wire instead of placing it themselves because radiologists are specifically trained to generate and interpret CT scans, fluoroscopy scans, and other types of imaging that are used to identify objects such as kidney stone. They are further skilled as conceptualizing the imagery information in three dimensional (3D) space to identify the location of an object such as a stone in that 3D space, and consequently are the most skilled at placing a guide wire according to that information.

To complete the PCNL, the urologist uses the placed guide wire to pass a deflated balloon or dilator along the wire. The urologist inflates the balloon or dilator to create a port large enough introduce a hollow suction tube, such as a nephrostomy tube, directly into the calyx of the kidney containing the stone. At this point a nephroscope or any one of a number of other instruments may be introduced into the suction tube to assist in removing the stone. For example, a stone breaker, laser, ultrasound, basket, grasper, drainage tube, etc. may be used to remove the stone or fragments thereof. Drainage tubes, such as nephrostomy catheters, may be deployed down the suction tube to reduce intra-renal pressure during and after the PCNL is completed.

PCNL is advantageous because it allows removal of larger stones than ureteroscopy, and it further allows for better flushing of leftover stone sediment, which helps reduce new stone formation and therefore decreases the frequency of similar follow up treatments being needed. However, PCNL is also a more aggressive treatment than ureteroscopy, requiring a minor surgery and a longer recovery period. Further, the common need for a radiologist to perform part of the procedure in conjunction with the urologist adds additional cost, complication, and operation scheduling time delay to a procedure that would ideally need only the urologist and their staff to perform. Further, PCNL requires the use of imaging techniques that are cumbersome and affecting on the persons involved in the procedure. For example, fluoroscopy requires the use of lead vests to reduce radiation uptake by hospital staff. Lead vests, however, do not eliminate all radiation, and are cumbersome to wear for long periods, and over the course of an entire career can cause orthopedic injury to the staff.

V.B. Process

To address these issues, the following section describes a new process for PCNL including an alignment sensor to identify the location of a stone or the target calyx of interest. FIGS. 10A-10E illustrate an example of this process where the alignment sensor is an electromagnetic (EM) sensor (or probe). In this process, the EM sensor is introduced into through the bladder BL into the ureter UTR and onward into the kidney KD. The EM sensor may be attached to a ureteroscope that includes an EM sensor 1010 proximal to the tip of the ureteroscope 1005. Alternatively, the EM sensor may be as simple as a coil connected to an electrical wire running the length of the ureteroscope which is connected to an external computing device configured to interpret electrical signals generated at the coil and passed down the wire.

V.B.I. Pre-Operative Segmentation & Planning

A pre-operative planning process may be performed in order to plan the procedure and navigation of the robotic tools. The process includes performing a pre-operative computerized tomography (CT) scan of the operative region. The resulting CT scan generates a series of two-dimensional images that are used to generate a three-dimensional model of the anatomical pathways and organs. The process of partitioning a CT image(s) into constituent parts may be referred to as "segmentation." The segmented images are then analyzed by the system 100 to identify the locations in three dimensional coordinate space of landmarks within or on the surface of the patient. For PCNL, this analysis may include identifying landmarks including any one or more of the skin, kidney stone(s), bone structures (e.g., ribs, vertebrae, pelvis, etc.), internal organs (e.g., kidneys, liver, colon, etc.), and external devices (e.g., skin patch sensor). After segmentation is complete, a means of localization (such as electromagnetic detection discussed below or intra-operative fluoroscopy) may be used in combination with the locations of identified landmarks and a registration method to provide a visual representation of the location of medical tools/instruments within the anatomy.

V.B.II. Electromagnetic Detection

Generally, an EM sensor, such as a coil, detect changes in EM fields as the operator moves the EM sensor 1010 in the kidney KD, for example by moving the ureteroscope tip while locating the stone ST. An implementation of the process using an EM sensor thus further includes a number of EM generators 1015 located externally to the patient. The EM generators 1015 emit EM fields that are picked up by the EM sensor 1010. The different EM generators 1015 may be modulated in a number of different ways so that when their emitted fields are captured by the EM sensor 1010 and are processed by an external computer, their signals are separable so that the external computer can process them each as a separate input providing separate triangulation location regarding the location of the EM sensor 1010, and by extension the location of the stone ST. For example, the EM generators may be modulated in time or in frequency, and may use orthogonal modulations so that each signal is fully separable from each other signal despite possibly overlapping in time. Further, the EM generators 1015 may be oriented relative to each other in Cartesian space at non-zero, non-orthogonal angles so that changes in orientation of the EM sensor will result in the EM sensor 1010 receiving at least some signal from at least one of the EM generators 1015 at any instant in time. For example, each EM generator may be, along any axis, offset at a small angle (e.g., 7 degrees) from each of two other EM generators. As many EM generators as desired may be used in this configuration to assure accurate EM sensor position information.

V.B.III. On-the-Fly Electromagnetic Registration

EM data is registered to an image of the patient captured with a different technique other than EM (or whatever mechanism is used to capture the alignment sensor's data), such as a CT scan, in order to establish a reference frame for the EM data. FIGS. 11A-11D show example graphs illustrating on-the-fly registration of an EM system to a segmented 3D model generated by a CT scan of a path through a tubular network (e.g., from the bladder into a ureter into one of the kidneys), according to one embodiment.

FIGS. 11A-11D show example graphs 1110-1140 illustrating on-the-fly registration of an EM system to a segmented 3D model of a path through a tubular network, according to one embodiment. In the example of FIG. 11A-11D, the EM sensor is attached to an endoscope tip 11101, however the principles of registration described with respect to these figures are equally applicable to the case where an EM sensor is attached to a guide wire and the 3D model is replaced with intra-operative fluoroscopy. In such an implementation, the 3D model discussed in the following sections is replaced with fluoroscopy that updates a representation of the patient in with each fluoroscopy update as the guide wire is progressed through the patient. Thus, insertion of the guide wire towards the kidney and registration of the guide wire to external EM generators occur at least partially simultaneously.

Figure 11A:
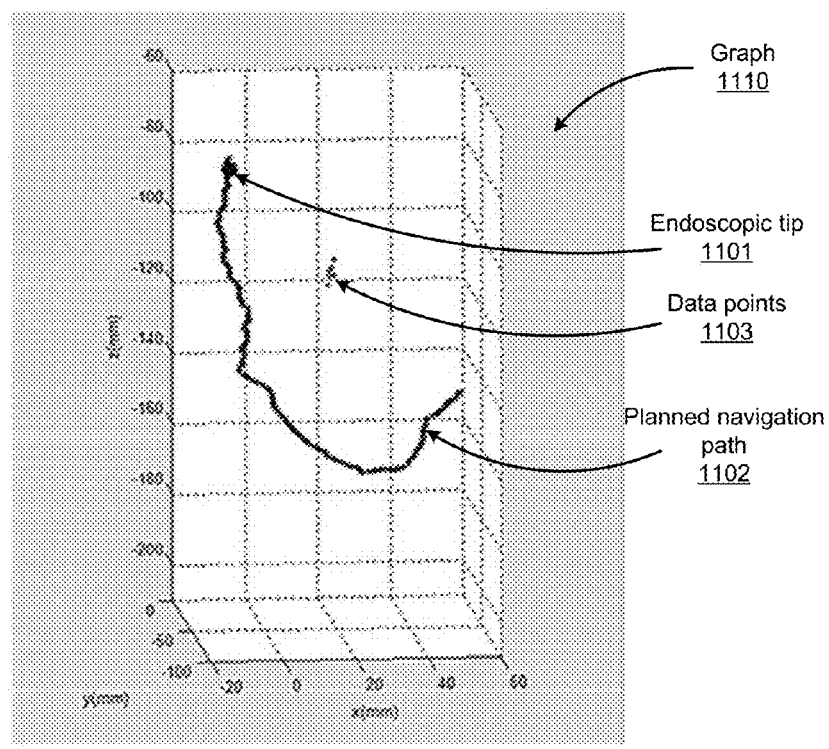
FIGS. 11A-11D show example graphs illustrating on-the-fly registration of an EM system to a 3D model of a path through a tubular network, according to one embodiment.

The navigation configuration system described herein allows for on-the-fly registration of the EM coordinates to the 3D model coordinates without the need for independent registration prior to an endoscopic procedure. In more detail, FIG. 11A shows that the coordinate systems of the EM tracking system and the 3D model are initially not registered to each other, and the graph 1110 in FIG. 11A shows the registered (or expected) location of an endoscope tip 1101 moving along a planned navigation path 1102 through a branched tubular network (not shown here), and the registered location of the instrument tip 1101 as well as the planned path 1102 are derived from the 3D model. The actual position of the tip is repeatedly measured by the EM tracking system 505, resulting in multiple measured location data points 1103 based on EM data. As shown in FIG. 11A, the data points 1103 derived from EM tracking are initially located far from the expected location of the endoscope tip 1101 from the 3D model, reflecting the lack of registration between the EM coordinates and the 3D model coordinates. There may be several reasons for this, for example, even if the endoscope tip is being moved relatively smoothly through the tubular network, there may still be some visible scatter in the EM measurement, due to breathing movement of the lungs of the patient.

The points on the 3D model may also be determined and adjusted based on correlation between the 3D model itself, image data received from optical sensors (e.g., cameras) and robot data from robot commands. The 3D transformation between these points and collected EM data points will determine the initial registration of the EM coordinate system to the 3D model coordinate system.

Figure 11B:
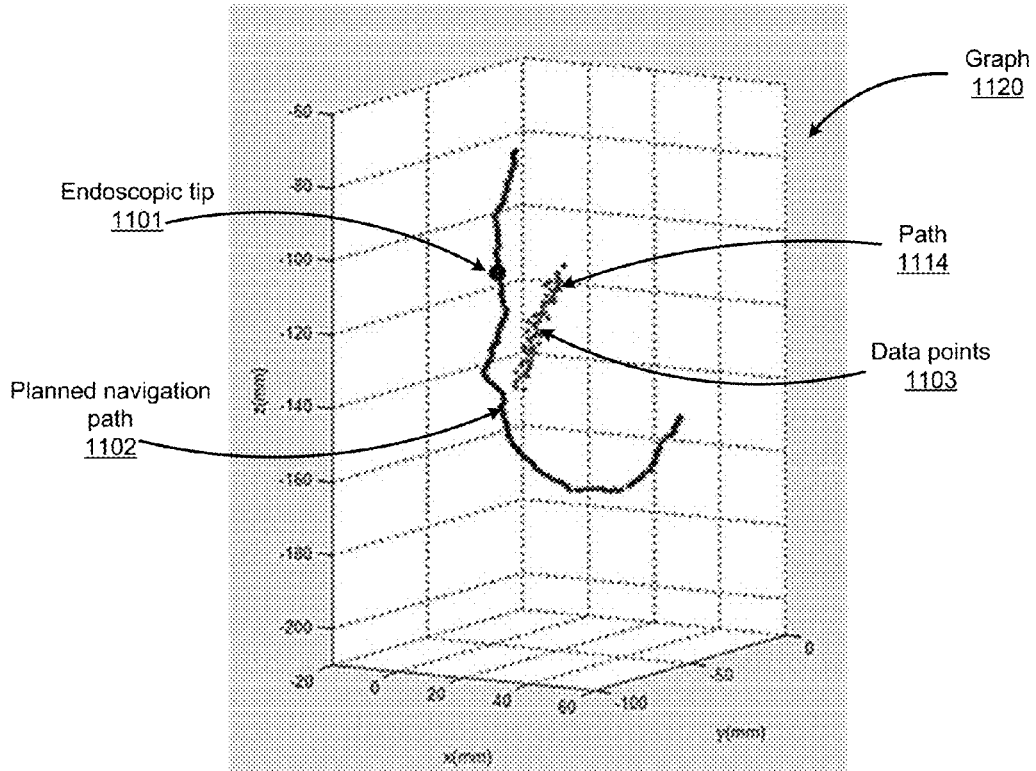

FIG. 11B shows a graph 1120 at a later temporal stage compared with the graph 1110, according to one embodiment. More specifically, the graph 1120 shows the expected location of the endoscope tip 1101 expected from the 3D model has been moved farther along the preplanned navigation path 1102, as illustrated by the shift from the original expected position of the instrument tip 1101 shown in FIG. 11A along the path to the position shown in FIG. 11B. During the EM tracking between generation of the graph 1110 and generation of graph 1120, additional data points 1103 have been recorded by the EM tracking system but the registration has not yet been updated based on the newly collected EM data. As a result, the data points 1103 in FIG. 11B are clustered along a visible path 1114, but that path differs in location and orientation from the planned navigation path 1102 the endoscope tip is being directed by the operator to travel along. Eventually, once sufficient data (e.g., EM data) is accumulated, compared with using only the 3D model or only the EM data, a relatively more accurate estimate can be derived from the transform needed to register the EM coordinates to those of the 3D model. The determination of sufficient data may be made by threshold criteria such as total data accumulated or number of changes of direction. For example, in a branched tubular network such as a bronchial tube network, it may be judged that sufficient data have been accumulated after arriving at two branch points.

Figure 11C:
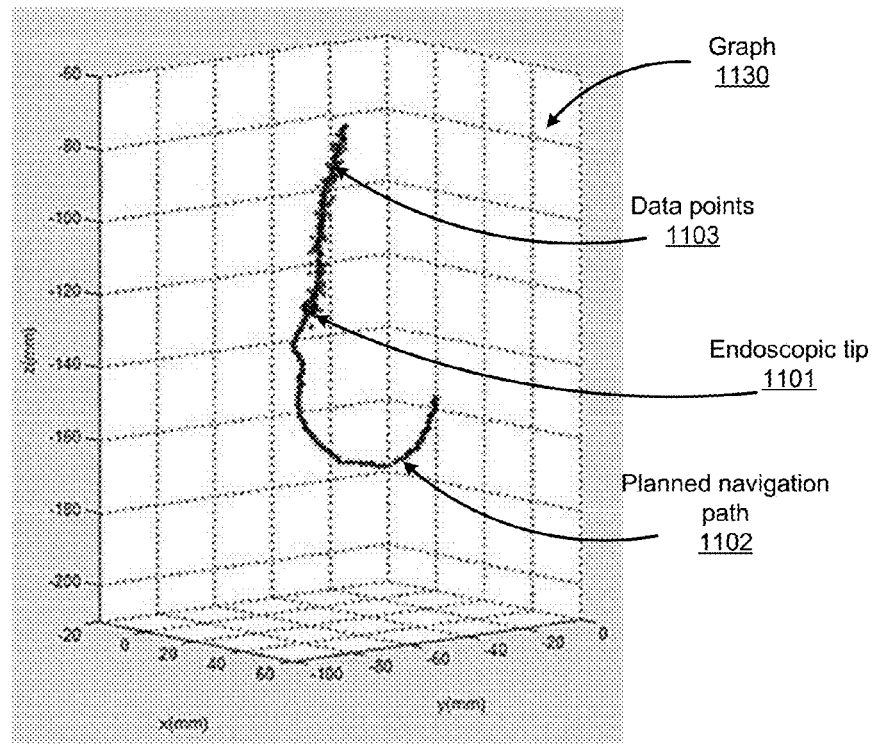

FIG. 11C shows a graph 1130 shortly after the navigation configuration system has accumulated a sufficient amount of data to estimate the registration transform from EM to 3D model coordinates, according to one embodiment. The data points 1103 in FIG. 11C have now shifted from their previous position as shown in FIG. 11B as a result of the registration transform. As shown in FIG. 11C, the data points 1103 derived from EM data is now falling along the planned navigation path 1102 derived from the 3D model, and each data point among the data points 1103 is now reflecting a measurement of the expected position of endoscope tip 1101 in the coordinate system of the 3D model. In some embodiments, as further data are collected, the registration transform may be updated to increase accuracy. In some cases, the data used to determine the registration transformation may be a subset of data chosen by a moving window, so that the registration may change over time, which gives the ability to account for changes in the relative coordinates of the EM and 3D models—for example, due to movement of the patient.

Figure 11D:
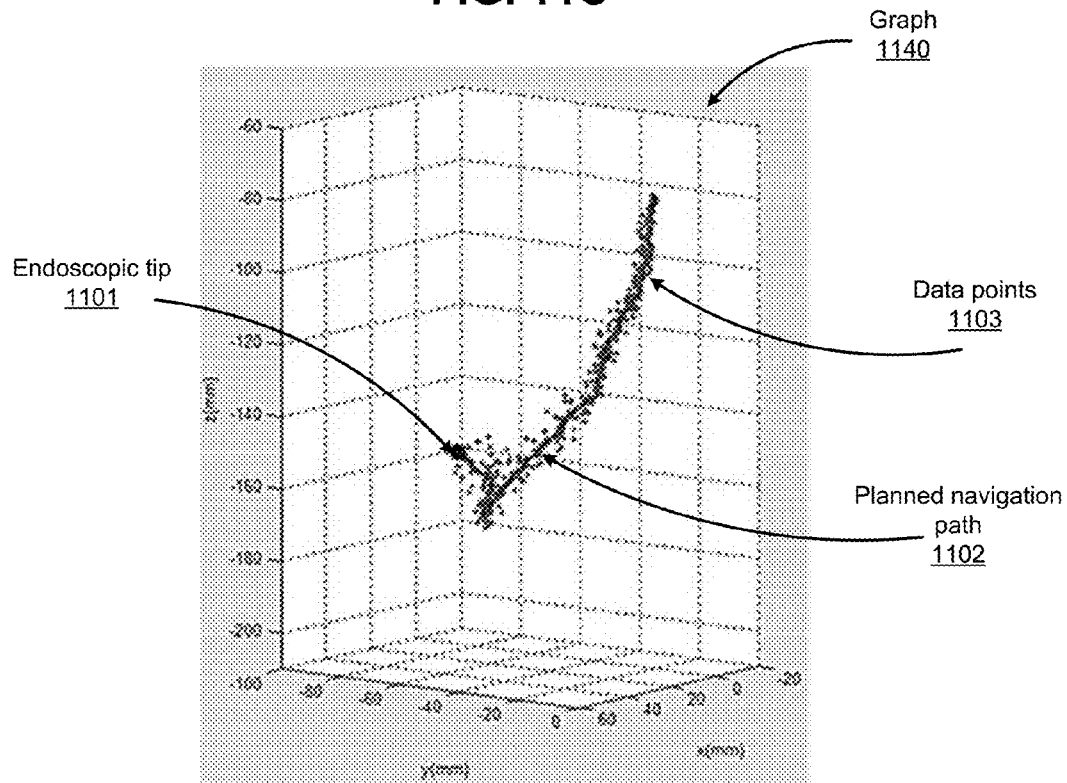

FIG. 11D shows an example graph 1140 in which the expected location of the endoscope tip 1101 has reached the end of the planned navigation path 1102, arriving at the target location in the tubular network, according to one embodiment. As shown in FIG. 11D, the recorded EM data points 1103 is now generally tracks along the planned navigation path 1102, which represents the tracking of the endoscope tip throughout the procedure. Each data point reflects a transformed location due to the updated registration of the EM tracking system to the 3D model.

Each of the graphs shown in FIGS. 11A-11D can be shown sequentially on a display visible to a user as the endoscope tip is advanced in the tubular network. Additionally or alternatively, the processor can be configured with instructions from the navigation configuration system such that the model shown on the display remains substantially fixed when the measured data points are registered to the display by shifting of the measured path shown on the display in order to allow the user to maintain a fixed frame of reference and to remain visually oriented on the model and on the planned path shown on the display.

V.B.IV Mathematical Analysis of Registration Transform

In terms of detailed analysis (e.g., mathematical analysis) and methods of the registration, in some embodiments, a registration matrix can be used to perform the registration between the EM tracking system and the 3D model, and as one example, the matrix may represent a translation and rotation in 6 dimensions. In alternative embodiments, a rotational matrix and a translation vector can be used for performing the registration.

$$M_1(\theta) = \begin{pmatrix} 1 & 0 & 0 \\ 0 & \cos\theta & \sin\theta \\ 0 & -\sin\theta & \cos\theta \end{pmatrix}$$

$$M_2(\varphi) = \begin{pmatrix} \cos\varphi & 0 & -\sin\varphi \\ 0 & 1 & 0 \\ \sin\varphi & 0 & \cos\varphi \end{pmatrix}$$

$$M_3(\psi) = \begin{pmatrix} \cos\psi & \sin\psi & 0 \\ -\sin\psi & \cos\psi & 0 \\ 0 & 0 & 1 \end{pmatrix}$$

From a perspective view of mathematical reasoning, as one example, applying a registration transform involves a shift from one coordinate system (x,y,z) to a new coordinate system (x',y',z') that may in general have its axes rotated to a different 3D orientation as well as having its origin shifted an arbitrary amount in each dimension. For example, a rotation to an azimuthal angle of radians θ may be expressed by the matrix $M_1$, a rotation to an inclination angle of φ radians may be expressed by the matrix $M_2$ etc., and further rotational matrices may be written as the product of rotation matrices. Similarly, a translation vector of (Δx Δy Δz) may be chosen to represent a translation of the origin in the x, y and z axes by Δx, Δy, and Δz respectively.

The registration transform may be determined by such methods as singular value decomposition on a cross correlation matrix between measured EM positions and estimated positions in the 3D model. The transformation matrix components may then be extracted from the decomposition, e.g., by identifying the appropriate principle components. An error signal may also be generated from the residuals of the determined transform, and the size of the error signal may be used to determine a level of confidence in the position. As further data are taken and the registration transform is determined more accurately, this error signal may decrease, indicating an increasing confidence in positions estimated in this manner.

V.B.V. Registration Method Using Rigid Landmarks

The registration process may additionally or alternatively incorporate a rigid homogenous transformation (4×4) containing a rotation matrix and a translation vector. This transformation is obtained by a registration of one or more point sets, typically by generating the point sets via single value decomposition (SVD), iterative closest point (ICP) algorithm, or another similar algorithm. For PCNL, generating point sets for input into these algorithms may involve performing a gross registration by (i) selecting, as a first point set, easily identifiable rigid landmarks such as ribs, ASIS of the pelvis, and vertebrae (e.g., those identifiable on the outside of the patient) from the pre-operative CT images during the segmentation process, and/or (ii) intraoperatively capturing these landmarks, as a second point set, with the EM localization system through navigating/touching the landmarks with an EM probe or pointer. The targeted kidney stone may also be used as a landmark. In the case of the kidney stone, the stone's location may be captured via a EM sensor enabled ureteroscope or an EM probe attached to a guide wire. In order to reduce registration error, certain landmarks may be weighted differently within the algorithm workflow. In cases where a kidney stone obstructs the renal pathways, registration using rigid landmarks may be used independently.

In one embodiment, the registration process may include intra-operatively capturing registration data using a combination of a handheld EM probe, such as an embedded or "clipped-on" EM-enabled sensor to identify identifiable external rigid landmarks, such as ribs, ASIS of pelvis, and vertebrae, that does not disturb the PCNL workflow. Calibration of the sensor or sensor-embedded device may be achieved by a pivot test resulting in the correlation between the sensor's position and the probe's tip. In some embodiments, the probe may take the form and functionality of a marker pen.

V.B.VI. Locating a Stone Based on EM and Camera Information

Referring back to FIG. 10A, once the EM sensor data has been registered to the CT scan and the EM-enabled ureteroscope tip or guide wire with EM sensor has been advanced into the kidney KD, the operator is able to move the ureteroscope tip (or guide wire) to identify the location of a stone within the kidney or other patient organ. In the case of a ureteroscope, recall from the description of the tip in Section I.C above with respect to FIG. 3C, the ureteroscope may include a camera for capturing images of the field of view (FOV) in front of the tip. Camera data captured as a video or sequence of images allows the operator to navigate the kidney to look for the stone. Simultaneously provided EM data from a distally coupled EM sensor in the ureteroscope identifies the location of the ureteroscope tip within the kidney.

In some embodiments, an EM probe or guide wire may be deployed down the working channel of the ureteroscope to provide additional EM measurements for alignment. After deployment, the EM probe or guide wire may be extended out of the working channel and past the distal tip of the ureteroscope in order to provide an additional EM measurement. The EM measurement from the EM probe or guide wire may be used in conjunction with the EM data from the distally-mounted EM sensor in the ureteroscope in order to generate a vector (including position and orientation information), which may be used to define a trajectory for the percutaneous needle access to the operative region.

Figure 10A:
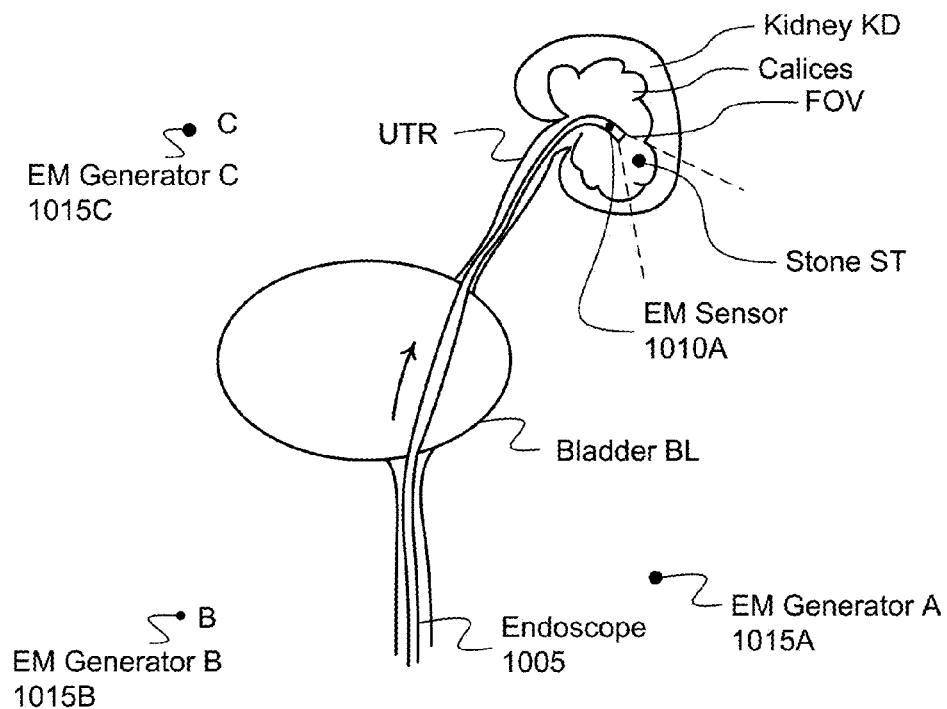
FIGS. 10A-10E illustrate an example of a PCNL process that includes a ureteroscope including an electromagnetic sensor to identify the location of a stone, according to one embodiment.
Figure 10B:
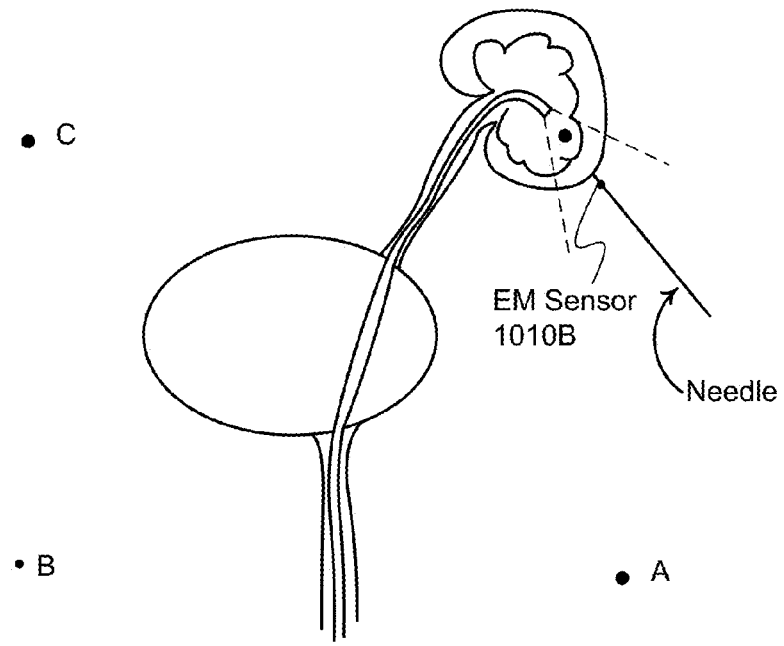

Once the stone has been located, for example by being present in the FOV of the camera on the tip, the percutaneous cut into the kidney can be performed. FIG. 10B illustrates the introduction of a needle to open a port from inside the kidney KD to outside of the patient, according to one embodiment. In this process, like the ureteroscope tip or guide wire, the needle also includes an alignment sensor such as an EM sensor. Similarly to the ureteroscope or guide wire, this may be a simple coil coupled to a wire running up the needle electrically coupled to the computer system. EM data received from the needle EM sensor may be received and processed similarly to ureteroscope tip or guide wire EM data as describe above.

Figure 10C:
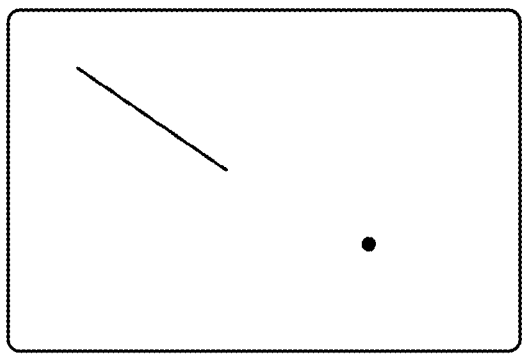
Figure 10D:
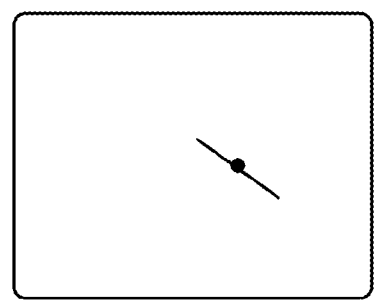

FIGS. 10C and 10D illustrate sample views of a graphical user interface 1060 for visually presenting needle and ureteroscope (or guide wire) EM data, according to one embodiment. The EM data from the needle and the EM data from the ureteroscope tip are processed together by the external computing system to generate a graphical user interface that can be displayed to the operator to facilitate their guiding of the needle towards the stone position, as indicated by the ureteroscope EM data. As illustrated in FIG. 10C, in one embodiment, the location of the needle, as provided by needle EM sensor data, is indicated by a first graphical element, such as a line on the graphical display 1060A, whereas the location of the stone, as indicated by ureteroscope EM data, is indicated by a second graphical element, such as a point. As illustrated in FIG. 10D, as the operator inserts the needle into the patient's body and moves it towards the stone, the needle graphic (line) will generally move closer to the stone graphic (point) on the display 1060B. The positions of the graphics over time will indicate whether the operator is successfully moving towards the stone, or whether they are drifting off target. At any point, the ureteroscope may be separately repositioned to re-center the stone within the FOV, move the ureteroscope closer to or further from the stone, or look at the stone from a different angle to facilitate alignment and motion of the needle towards the stone.

The needle's motion may be constrained by the surgical robotics system performing the process or by design. For example, if the needle contains only a single EM sensor, the needle may not be able to provide information about the roll of the needle about its long axis. In this case, the needle will generally be able to move in 5 degrees of freedom (in/out, pitch +/−, yaw +/−, but not roll). In one embodiment, the X, Y, and Z axes of the system (and subsequently, through the GUI, the user) of the location of the tip of the needle in space relative to the target (ureteroscope tip) and relative to the anatomy (pre-operative CT that has been registered with the EM space and actual patient anatomy). The pitch and yaw of the needle tip informs the system of the current heading of the needle. With this information the system is able to project a predicted path onto the GUI to help the physician align the needle as he continues inserting it towards the target.

In other embodiments, additional EM sensors or other types of alignment sensor may be added more degrees of freedom may be permitted to the needle's motion. In yet other embodiments, the needle may be manually delivered by the physician using the guidance provided through the robotic system's GUI. For example, the introduction of a second EM sensor in the needle that oriented at a non-zero angle with respect to the first EM sensor can provide a roll degree of freedom, and the surgical robotics system 100 may be configured or designed to allow the operator to make a roll motion.

In addition to the basic GUI introduced above, additional graphical or auditory notifications may be provided to indicate that the needle has been positioned sufficiently close to the stone, that the needle has entered the kidney, that the needle has drifted sufficiently far off course, or any other trigger condition that may be warranted or requested by the operator. These notifications may change a color of the graphical user interface, sound a tone, or otherwise. The basic GUI may also be more comprehensive than illustrated in FIGS. 10C and 10D. It may also include an outline of the kidney, which will appear differently based on the orientation in 3D space of the ureteroscope tip and needle. It may further include outlines of the calices of the kidney and/or vasculature surrounding the kidney, as well as outlines of other organs or critical anatomy.

Figure 10E:
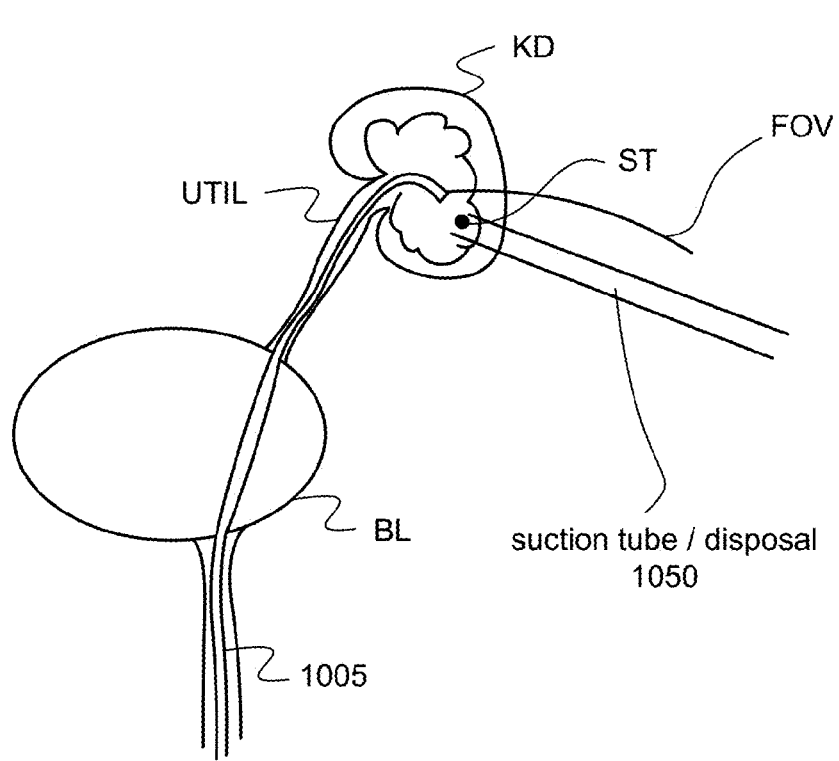

FIG. 10E illustrates a point in the PCNL procedure where the needle has penetrated the kidney near the stone, according to one embodiment. Once the needle has reached the stone, a balloon may be used to inflate the port, and a suction tube 1050 may be introduced to provide access to the kidney for insertion of larger diameter tools.

The PCNL process described above may be accomplished manually. Generally, the ureteroscope may be positioned first near the stone by a first operator. The same or a different operator may then insert the needle using the internal EM-sensor (via ureteroscope or guide wire) as a guide. In some embodiments, the EM sensor may be used to place a fiducial or beacon to assist the physician to return to the location of the stone or calyx, so that the endoscope or guide wire can be removed and does not need to be left in the patient to accomplish the same purpose. Alternatively, manipulation of the ureteroscope, guide wire, and needle may be accomplished by a surgical robotics system 100.

In an alternative embodiment, rather than using two different "live" alignment sensors attached to the needle and ureteroscope or guide wire as described above, the PCNL process may be carried out using only a single "live" alignment sensor attached to the needle. In one version of this embodiment, the EM system is registered using a pen or other another implement located outside the body with an attached EM sensor. The pen is used to identify landmarks of the patient's anatomy, and is rotated to register with respect to the EM generators. With this registration and landmark information, an operator or the surgical robotics system is oriented with respect to the patient's anatomy. Subsequently, the needle can be navigated towards the kidney (or other cavity) based on data provided by the EM sensor located in the needle, the landmark location information, and the registration information. An advantage of this approach is that it removes the need for separate navigation of an instrument with an EM sensor into the patient in order to determine where to direct the needle. The loss of precision provided by the EM sensor close to the stone or other object can be at least partially compensated for by the landmark registration process.

The advantages of the above-described process for placing the needle and associated port are numerous. Navigation of the needle is made less skill intensive using the ureteroscope or guide wire as a guide. A single operator or robotic system may carry out the process. Fluoroscopy can be omitted if desired.

Although the above process has been described with the alignment sensor being an EM sensor (and associated EM generators), in practice other kinds of positioning sensors may be used instead. Examples include, but are not limited to, accelerometers and gyroscopes, magnetometers, fiber optic shape sensing (e.g., via Bragg gratings, Rayleigh scattering, interferometry, or related techniques), etc. Depending on the implementation, registration to a separate form of patient imagery, such as a CT scan, may or may not be necessary to provide a frame of reference for locating stones within the patient.

Further, this process may be used in other operations beyond PCNL, such as gallbladder stone removal, lung (pulmonary/transthoracic) tumor biopsy. Generally, any type of percutaneous procedure may be performed by using an endoscope with an alignment sensor and a needle with a similar alignment sensor. In each of these processes, the alignment sensor-equipped endoscopic tip entered through a patient cavity into a patient organ provides a guide for the insertion of the alignment sensor-equipped needle. Additional examples include stomach operations, esophagus and lung operations, etc. Further, the objects to be removed do not necessarily need to be urinary stones, they may be any object, such as a foreign body or object created within the human body.

V.B.V. Stone and Fragment Removal

With the suction tube in place, a variety of techniques may be used to remove a stone. Various instruments may be inserted into the suction tube or ureteroscope to break up or remove the stone and stone fragments. Examples include the basket apparatus described above, a laser or optical fiber to break up stones via lithotripsy, an ultrasound device to break up stones via shockwaves, a blender, chisel, or drill to break up stones mechanically, and so on. Alternatively, the various instruments described above may be coupled or integrated into the suction tube in order to assist in the breaking up of kidney stone fragments and debris to assist aspiration using the suction tube.

In one embodiment, once the suction tube is in place and given that the ureteroscope is already in place near the stone, any other instrument taking up the working channel is retracted from that ureteroscope. This may, for example, be the EM sensor itself or another instrument. A basket apparatus, such as the one described above in Section III, or another grasping tool, i.e., grasper, may then be inserted into the working channel of the ureteroscope. and is extended out past the ureteroscope tip near the stone.

The basket apparatus (or other similar device) may be used to capture the stone and place it near the opening at the distal end of the suction tube within the patient organ, where instruments coupled to the suction tube, deployed down the suction tube, or deployed down the working channel of the ureteroscope may break up the stone in order to assist aspiration of the material down the suction tube. Additionally or alternatively, lithotripsy may be performed (using a laser tool inserted through the working channel of the basket apparatus, ureteroscope, or deployed down or attached to the suction tube) to break up the stone so that it can be sized to fit through the suction tube.

During the procedure, suction (negative pressure) may be applied down the suction tube in order to aspirate the stone or any stone fragments that are generated, while the ureteroscope or basket apparatus continuously irrigates the operative area. Simultaneous irrigation and suction helps maintain pressure in the patient cavity. In embodiments where the ureteroscope may comprise of both a sheath component and a leader component, i.e., a leaderscope, the irrigation fluid may be provided through the working channel of the sheath component, in order for the working channel of the leader component to remain available for tool deployment, such as a basket apparatus or a grasper, to help position and move the stone into closer proximity to the suction tube for aspiration.

Consequently, any instruments extending out of the ureteroscope and the suction on the suction tube operate in tandem to allow capture and removal of the stone or stone fragments from the kidney. Due to the presence of both the suction tube and the surgical tool, whether it be a basket apparatus or other grasping tool, the removal of the stone effectively proceeds as if the operator had two "hands" present within the kidney to deal with the removal of the stone, along with simultaneous vision of the operating area as provided by the camera on the tip of the ureteroscope.

VI. Additional Considerations

The processes described above, particularly those for controlling the arms of the surgical robotics system, processing alignment sensor data to generate position and orientation information for the alignment sensor and/or needle, and for generating a graphical user interface to display this information may all be embodied in computer program instructions stored within a non-transitory computer-readable storage medium, and designed to be executed by one or more computer processors within one or more computing devices. The non-transitory computer-readable medium can be stored on any suitable computer readable media such as RAMs, ROMs, flash memory, EEPROMs, optical devices (CD or DVD), hard drives, floppy drives, or any suitable device. The computer-executable component is preferably a processor but the instructions may alternatively or additionally be executed by any suitable dedicated hardware device.

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A method for capturing an object in a cavity comprising:
   advancing an endoscope into the cavity comprising the object;
   advancing a basket tool through a working channel of the endoscope to open the basket tool within the cavity, wherein the basket tool is formed of a plurality of pull wires, that extend outside the cavity with each pull wire coupled to a different rotatable body to individually actuate each and wherein advancing the basket tool through the working channel of the endoscope to open the basket tool within the cavity comprises translating one or more of the pull wires distally along a longitudinal axis of the endoscope to increase the size of the basket tool within the cavity;
   positioning the basket tool to enclose the object by selectively actuating the rotatable body to selectively unspool and spool associated pull wires to reposition the basket tool around object; and
   collapsing the basket tool while simultaneously advancing the basket tool forward so that the object remains within the basket tool as it closes around the object.

2. The method of claim 1 wherein advancing the basket tool forward comprises:
   advancing the endoscope further into the cavity, thereby also advancing the basket tool further into the cavity.

3. The method of claim 1 further comprising retracting the basket holding the object out of the cavity.

4. The method of claim 1 wherein collapsing the basket tool comprises:
   actuating the rotatable bodies to spool the pull wires thereby decreasing the size of the basket tool within the cavity.

5. The method of claim 1 wherein advancing the endoscope into the cavity comprising the object comprises:
   actuating at least one instrument base or a first robotic arm controlling motion of at least one of a sheath and a leader of the endoscope.

6. The method of claim 5 wherein advancing the basket tool through the working channel of the endoscope to open the basket tool within the cavity comprises:
   actuating at least one of a tool base or a second robotic arm controlling the motion of the basket tool along a long axis of the basket tool and endoscope.

7. The method of claim 5 wherein positioning the basket tool to enclose the object comprises:
   actuating at least one of a tool base and a second robotic arm controlling the motion of the basket tool along a long axis of the basket tool and endoscope.

8. The method of claim 7 wherein simultaneously advancing the basket tool forward comprises:
   actuating at least one of a second and a third instrument base or a third robotic arm to move at least one of the leader and the basket tool, respectively, further into the cavity.

9. The method of claim 7 wherein simultaneously advancing the basket tool forward comprises:
   actuating at least one of a second and a third instrument base or a third robotic arm to move one of the sheath and leader relative to each other, to move the basket tool further into the cavity.

10. The method of claim 1 wherein advancing the endoscope into the cavity comprising the object comprises:
    actuating an instrument base coupled to the endoscope or a first robotic arm coupled to the instrument base, wherein the first robotic arm is configured to control motion the endoscope.

11. The method of claim 10 wherein advancing the basket tool through the working channel of the endoscope to open the basket tool within the cavity comprises:
    actuating a tool base coupled to the basket tool or a second robotic arm coupled to the tool base, wherein the second robotic arm is configured to control motion of the basket tool along a long axis of the basket tool and the endoscope.

12. The method of claim 10 wherein positioning the basket to enclose the object comprises:
    actuating a tool base coupled to the basket tool or a second robotic arm coupled to the tool base, wherein the second robotic arm is configured to control motion of the basket tool along a long axis of the basket tool and the endoscope.

13. The method of claim 12 wherein collapsing the basket tool while simultaneously advancing the basket tool forward comprises:
    actuating at least one of the tool base and the second robotic arm to retract the basket tool into the endoscope; and
    actuating at least one of the instrument base and the first robotic arm to move the endoscope further into the cavity.

14. The method of claim 12 wherein collapsing the basket tool while simultaneously advancing the basket tool forward comprises:
    actuating at least one of the tool base, the instrument base, the first robotic arm and the second robotic arm to move the basket tool and the endoscope in opposite directions relative to each other.

15. The method of claim 1,
    wherein the endoscope comprises a sheath component coupled to a first robotic arm, and a leaderscope coupled to a second robotic arm, and
    wherein the basket tool is coupled to a third robotic arm.

16. The method of claim 15 wherein advancing the endoscope into the cavity comprising the object comprises:

actuating at least one of the first robotic arm and second robotic arm to move the basket tool further into the cavity.

17. The method of claim 15 wherein advancing the basket tool through the working channel of the endoscope to open the basket tool within the cavity comprises:
   actuating the third robotic arm to control motion of the basket tool along a long axis of the basket tool and the endoscope.

18. The method of claim 15 wherein positioning the basket to enclose the object comprises:
   actuating a tool base coupled to the basket tool or the third robotic arm coupled to the tool base, wherein the third robotic arm is configured to control motion of the basket tool along a long axis of the basket tool and the endoscope.

19. The method of claim 18 wherein collapsing the basket tool while simultaneously advancing the basket tool forward comprises:
   actuating at least one of the tool base and the third robotic arm to retract the basket tool into the endoscope; and
   actuating at least one of the first robotic arm and the second robotic arm to move the endoscope further into the cavity.

20. The method of claim 18 wherein collapsing the basket tool while simultaneously advancing the basket tool forward comprises:
   actuating at least one of the tool base, the third robotic arm, the first robotic arm, and the second robotic arm to move the basket tool and the endoscope in opposite directions relative to each other.

21. The method of claim 1 further comprising:
   passing an optical fiber or a laser through a working channel of the basket tool; and
   activating the optical fiber or laser perform lithotripsy on the object to break it apart.

22. The method of claim 1 further comprising:
   passing a mechanical drill through a working channel of the basket tool; and
   activating the drill in contact with the object to break it apart.

23. The method of claim 1 further comprising:
   passing a chisel through a working channel of the basket tool;
   activating the chisel in contact with the object to break it apart.

24. The method of claim 1 further comprising:
   passing fluid through a working channel of a basket tool towards the object to break it apart.

25. The method of claim 1 wherein the object is at least one from the group consisting of: a kidney stone or a bladder stone, a stone formed from at least one of calcium, magnesium, ammonia, uric acid, and cysteine.

26. The method of claim 1 wherein the cavity is a kidney of a patient or a calyx within the kidney of the patient.

27. The method of claim 1 wherein the endoscope is a ureteroscope.

* * * * *

UNITED STATES PATENT AND TRADEMARK OFFICE
CERTIFICATE OF CORRECTION

| | | |
|---|---|---|
| PATENT NO. | : 9,949,749 B2 | Page 1 of 1 |
| APPLICATION NO. | : 15/339476 | |
| DATED | : April 24, 2018 | |
| INVENTOR(S) | : David Paul Noonan et al. | |

It is certified that error appears in the above-identified patent and that said Letters Patent is hereby corrected as shown below:

In the Specification

In Column 1, Line 24, change "may formed" to --may be formed--

In Column 1, Line 25, change "ur" to --uric--

In Column 3, Line 16, change "5F and" to --5F--

In Column 18, Line 4, change "as" to --at--

In Column 19, Line 55 (Approx.), change "FIG." to --FIGS.--

In Column 19, Line 57 (Approx.), change "11101," to --1101,--

In Column 25, Line 36 (Approx.), change "V.B.V." to --V.B.VII.--

In Column 25, Line 57, change "ureteroscope. and" to --ureteroscope and--

In the Claims

In Column 28, Line 29 (Approx.), Claim 10, change "motion the" to --motion of the--

In Column 30, Line 6, Claim 21, change "laser perform" to --laser to perform--

Signed and Sealed this
Fifteenth Day of January, 2019

Andrei Iancu
*Director of the United States Patent and Trademark Office*